(12) United States Patent
Iyengar et al.

(10) Patent No.: US 7,090,764 B2
(45) Date of Patent: Aug. 15, 2006

(54) METHOD AND APPARATUS FOR PROCESSING ELECTROCHEMICAL SIGNALS

(75) Inventors: Sridhar G. Iyengar, Somerville, MA (US); Daniel Haas, Cambridge, MA (US); Craig Bolon, Brookline, MA (US)

(73) Assignee: Agamatrix, Inc., Salem, NH (US)

( * ) Notice: Subject to any disclaimer, the term of this patent is extended or adjusted under 35 U.S.C. 154(b) by 639 days.

(21) Appl. No.: 10/342,794

(22) Filed: Jan. 15, 2003

(65) Prior Publication Data

US 2003/0178322 A1    Sep. 25, 2003

Related U.S. Application Data

(60) Provisional application No. 60/350,175, filed on Jan. 15, 2002.

(51) Int. Cl.
*G01N 27/26* (2006.01)
*G01N 27/416* (2006.01)
*G01N 31/00* (2006.01)
*C12Q 1/00* (2006.01)

(52) U.S. Cl. .............. 205/775; 205/777.5; 702/23

(58) Field of Classification Search ..............
204/403.4–403.15, 416–419, 433, 431; 205/775, 205/777.5, 778, 778.5, 779, 787, 787.5, 789, 205/789.5, 790.5, 791, 792, 793.5, 794; 702/19, 702/22, 23
See application file for complete search history.

(56) References Cited

U.S. PATENT DOCUMENTS

| 4,631,116 A | 12/1986 | Ludwig | 204/1 |
|---|---|---|---|
| 4,725,339 A | 2/1988 | Bindra et al. | 204/1 |
| 4,805,624 A | 2/1989 | Yao et al. | 128/635 |
| 5,124,011 A | 6/1992 | Rogers et al. | 204/153.1 |
| 5,192,403 A | 3/1993 | Chang et al. | 204/153.1 |
| 5,292,423 A | 3/1994 | Wang | 204/434 |
| 5,468,366 A | 11/1995 | Wegner et al. | 204/403 |
| 5,650,061 A | 7/1997 | Kuhr et al. | 205/775 |
| 5,707,799 A | 1/1998 | Hansmann et al. | 435/6 |
| 5,958,215 A | 9/1999 | Kuhr et al. | 205/787 |
| 5,980,708 A | 11/1999 | Champagne et al. | 204/406 |

(Continued)

FOREIGN PATENT DOCUMENTS

EP    1081490 A1    3/2001

(Continued)

OTHER PUBLICATIONS

JPO English language computer translation of Figaro Giken KK □□(JP 2867474 B2.*

(Continued)

*Primary Examiner*—Alex Noguerola
(74) *Attorney, Agent, or Firm*—Marina Larson & Associates, LLC

(57) ABSTRACT

Systems and methods are provided herein for improving the selectivity and productivity of sensors via digital signal processing techniques. According to one illustrative embodiment, in an electrochemical method for monitoring of a select analyte in a mixed sample with an interfering analyte, an improvement is provided that includes applying a large amplitude potential stimulus waveform to the sample to generate a nonlinear current signal; and resolving a signal contribution from the select analyte in the generated signal by a vector projection method with an analyte vector comprising a plurality of real and imaginary parts of one or more Fourier coefficients at one or more frequencies of a reference current signal for the select analyte.

36 Claims, 18 Drawing Sheets

U.S. PATENT DOCUMENTS

| | | | |
|---|---|---|---|
| 6,007,775 A | 12/1999 | Yager | 422/57 |
| 6,294,392 B1 | 9/2001 | Kuhr et al. | 436/518 |
| 2004/0157338 A1 | 8/2004 | Burke et al. | |
| 2004/0157339 A1 | 8/2004 | Burke et al. | |
| 2005/0069892 A1 | 3/2005 | Iyengar et al. | 435/6 |
| 2005/0093556 A1* | 5/2005 | Mueller et al. | 324/693 |

FOREIGN PATENT DOCUMENTS

| | | |
|---|---|---|
| EP | 1143240 | 10/2001 |
| EP | 1143240 A1 | 10/2001 |
| JP | 2867474 B2 * | 12/1998 |
| WO | WO 97/39343 | 10/1997 |

OTHER PUBLICATIONS

CAPLUS abstract of Green et al. ("Signal-to-noise assessment of eigenvectors based on cross-validation," Book of Abstracts, 219th ACS National Meeting, San Francisco, CA, Mar. 26-30, 2000).*

CAPLUS abstract of Fairchild et al. ("PCR eigenvector selection based on correlation relative standard deviations," Journal of Chemometrics (2001), 15(7), 615-625).*

Holmin et al., Compression of electronic tongue data based on voltammetry—a comparative study, 2001, pp. 455-464, vol. 76, No. 1-3, Publisher: Sensors and Actuators B, Elsevier Sequoia S.S., Lausanne, CH: XP004241157.

Long et al., Voltammetry in Static and Flowing Solutions with a Large-Amplitude Sine Wave Potential, 1992, pp. 429-437, vol. 4, Publisher: VHC Publishers, Inc., US.

Zhong et al., The discrete wavelet neural network and its application in oscillographic chronopotentiometric determination, 2001, pp. 67-74, vol. 59, No. 1-2, Publisher: Chemometrics and intelligent laboratory systems, elsevier science publishers B.V., Amsterdam, NL.

Singhal, et al., "Sinusoidal Voltammetry for the Analysis of Carbohydrates at Copper Electrodes", Anal. Chem. Apr. 15, 1997, vol. 69, No. 8, pp. 1662-1668.

Fung, et al., "Application of Dual-Pulse Staircase Voltammetry for Simultaneous Determination of Glucose and Fructose", Electroanalysis 1995, 7, No. 2, pp. 160-165.

Cullison, et al., "Cyclic Voltammetry with Harmonic Lock-In Detection: Applications to Flow Streams", Electroanalysis 1996, 8, No. 4, pp. 314-319.

Brazill, et al., "Sinusoidal voltammetry: a frequency based electrochemical detection technique", Journal of Electroanalytical Chemistry 531 (2002) 119-132.

Nakata, et al., "Discrimination of Glucose from Its Interferences Using an Amperometric Sensor Based on Electrochemical Nonlinearity", Anal. Chem. 1998, 70, 4304-4308.

Lupu, et al., "Polythiophene Derivative Conducting Polymer Modified Electrodes and Microelectrodes for Determination of Ascorbic Acid. Effect of Possible Interferents", Electroanalysis 2002, 14, No. 7-8.

Iyengar, et al., "Applying Immittance Spectroscopy to Monitoring Hydrogen Peroxide in the Presence of Ascorbic Acid. Part I: Theoretical Considerations", Electoanalysis 2001, 13, No. 6.

Iyengar, et al., "Phasor Transform To Extract Glucose And Ascorbic Acid Data In An Amperometric Sensor", Analyst, 2000, 125, 1987-1992.

Iyengar, et al., "Selective Monitoring of the Hydrogen Peroxide Signal in the Presence of Ascorbic Acid. Part II: Preliminary Practical Realization of Applying Immittance Spectroscopy", Electroanalysis 2001, 13, No. 7.

Iyengar, et al., "Frequency Domain Selection of the Peroxide Signal for Amperometric Biosensors", Electroanalysis 1998, 10, No. 16.

Iyengar, et al., "Data from overlapping signals at an amperometric electrode using admittance vectors", Journal of Electroanalytical Chemistry 521 (2002) 61-71.

* cited by examiner

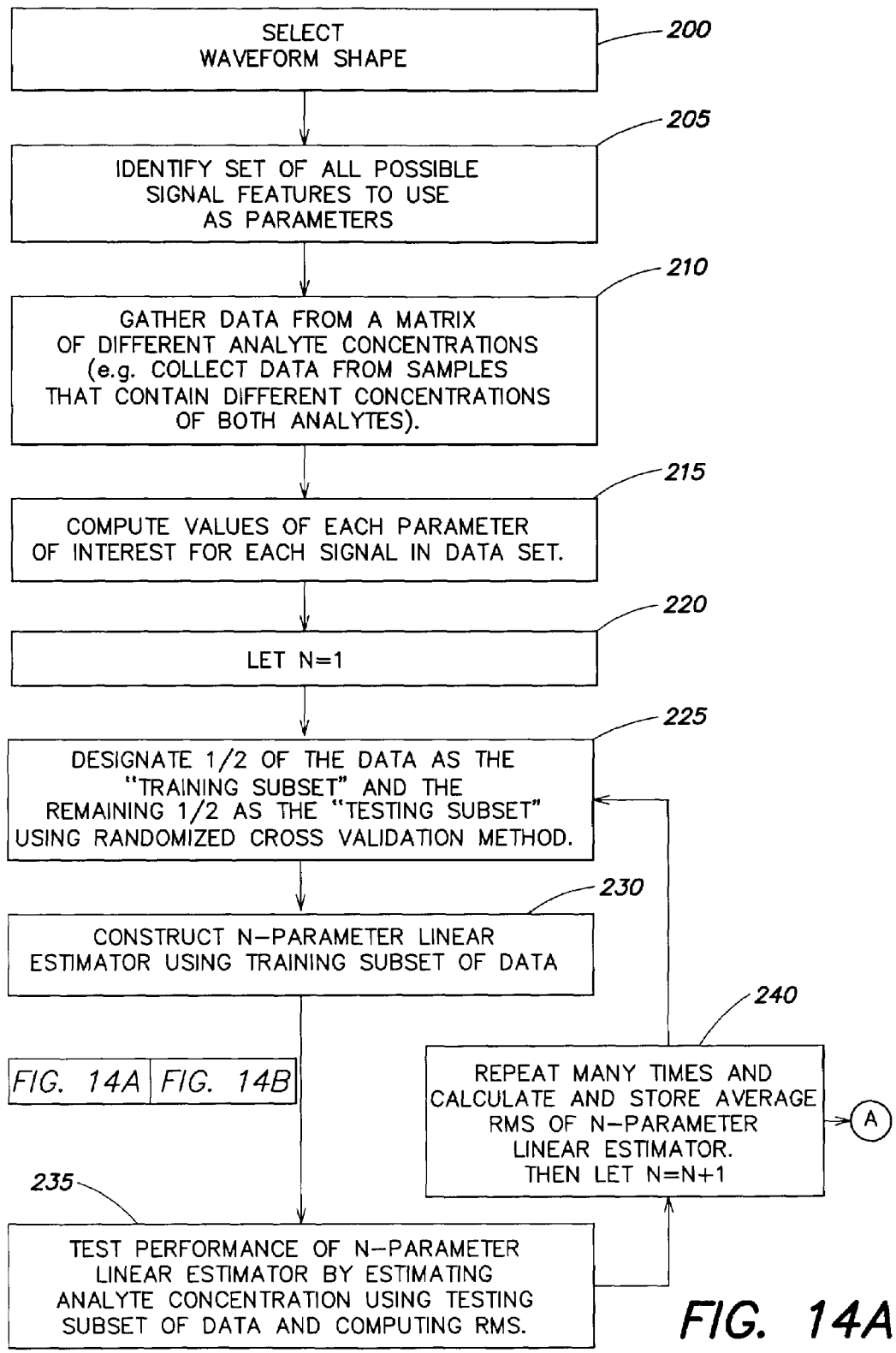

| [GLUCOSE] (mM) | [ASCORBIC ACID] (mM) | | | | | | | | | |
|---|---|---|---|---|---|---|---|---|---|---|
| | 0 | .1 | .2 | .3 | .5 | 1 | 1.5 | 2 | 3 | 4 |
| 0 | X | X | X | X | X | X | X | X | X | X |
| 1 | X | X | X | X | X | X | X | X | X | X |
| 2 | X | X | X | X | X | X | X | X | X | X |
| 3 | X | X | X | X | X | X | X | X | X | X |
| 4 | X | X | X | X | X | X | X | X | X | X |
| 5 | X | X | X | X | X | X | X | X | X | X |
| 7 | X | X | X | X | X | X | X | X | X | X |
| 10 | X | X | X | X | X | X | X | X | X | X |
| 12 | X | X | X | X | X | X | X | X | X | X |
| 15 | X | X | X | X | X | X | X | X | X | X |
| 20 | X | X | X | X | X | X | X | X | X | X |
| 25 | X | X | X | X | X | X | X | X | X | X |
| 30 | X | X | X | X | X | X | X | X | X | X |

FIG. 15

METHOD AND APPARATUS FOR PROCESSING ELECTROCHEMICAL SIGNALS

This application claims priority to provisional application 60/350,175, filed Jan. 15, 2002.

BACKGROUND OF THE INVENTION

Since their advent in the 1960s, the use of biosensors has become widespread. A biosensor is a device that couples a biological recognition element (e.g., an enzyme or antibody), with a transducer (e.g., an electrode or photodiode), to convert biochemical information into an electric signal.

FIG. 1 shows the action of a glucose biosensor that includes an enzyme coated electrode 1 to which a voltage potential is applied. The biosensor of FIG. 1 is an example of amperometric detection in which a voltage is applied to the electrode 1 which causes a particular analyte (the substance being measured) in the sample to oxidize or (i.e., give up electrons to the electrode). The oxidation cause a current 3 to be generated which can then be detected and analyzed. The potential at which the analyte oxidizes is called the "oxidation potential" of the analyte.

Generally speaking, the term "redox potential" is used to indicate the potential at which an analyte is either oxidized or reduced. In the biosensor of FIG. 1, glucose ("GLU") reacts with the enzyme and transfers electrons to the enzyme, converting it from its oxidized state to its reduced state. Some other electron shuttle (in an oxidized form) reacts with the enzyme to turn it back over to its oxidized state. The electron shuttle then becomes reduced in the process (taking electrons from the reduced enzyme). The reduced electron shuttle is what is oxidized at the electrode. One example of such an electron shuttle is oxygen, being reduced to hydrogen peroxide. There is also a family of electron shuttles called mediators that are used in many commercial glucose test strips that perform this function instead of relying on oxygen.

Using the technique of amperometry, selectivity towards one of several analytes in a sample is achieved by applying the redox potential of that analyte. Thus, in FIG. 1, a sufficiently high potential is being applied to oxidize the reduced electron shuttle, and the resultant current 3 detected by the electrode depends on the concentration of the reduced electron shuttle, which in turn depends on the glucose concentration in the sample. (It should be noted that in actuality a mediator agent associated with the glucose is reoxidized and reacts with the reduced enzyme. The concentration of the reduced mediator is directly indicative of the concentration of glucose in the sample. For the sake of simplicity glucose will be referred to as the analyte being oxidized with the understanding that it is in fact the reduced mediator that is the actual analyte detected at the electrode.)

Electrochemical biosensors are an attractive offering due to their low cost and ease of manufacture, however other blood chemicals, such as ascorbic acid (vitamin C), acetaminophen ("TYL" in FIG. 1), and uric acid can interfere with the biosensor action resulting in erroneous readings. FIG. 1 shows the effect of the interferent ascorbic acid ("C"), in which a molecule of ascorbic acid 5 has diffused through the enzyme layer, been directly oxidized by the electrode 1, and generated a current 7.

Thus, when a sample contains several analytes, all with overlapping redox potentials (that is, where the redox potentials of several analytes are within the same ranges and thus all give rise to a redox current at the same applied electrode potential), the selectivity of the electrode diminishes. The current generated at the electrode results from all analytes from the sample that can be electro-oxidized or electro-reduced at the given electrode potential, resulting in a sensed current that includes unknown components of each analyte, thereby resulting in diminished electrode selectivity and incorrect concentration readings. Testing for an analyte without accounting for analytes with overlapping redox potentials will result in inaccurate readings.

FIGS. 2–4 graphically illustrate the foregoing problem, with respect to hydrogen peroxide (the target analyte) and ascorbic acid (the interferent). As shown in FIGS. 2 and 3, increasing amounts of each of ascorbic acid and hydrogen peroxide (x-axis) when applied with the same DC amperometric voltage of 600 mV generate an increase in the sensed current (y-axis). Calibration curves 9 and 11 are determined from current readings 13 and 15, respectively.

Because the redox potentials overlap at 600 mV, false readings result as shown in FIG. 4, when testing for hydrogen peroxide. The tester should read a concentration of 1 mM, as indicated by dashed line 17. The tester instead falsely generates readings 19 showing increasing amounts of hydrogen peroxide when in fact increasing amounts of ascorbic acid are added to the measured sample containing a constant amount of hydrogen peroxide.

Other interferences that commonly plague biosensors include cross-reactivity with other sample components, physical deterioration or fouling of the sensor, or background noise. Efforts to overcome the foregoing shortcomings of biosensors have traditionally been to use physical or chemical enhancements to the device such as using chemical mediators or perm-selective membranes. However, mediators can contribute to increased background noise and membranes add unnecessary production costs while reducing the sensor's overall sensitivity.

SUMMARY OF THE INVENTION

Systems and methods are provided herein for improving the selectivity and productivity of sensors via digital signal processing techniques. According to one illustrative embodiment, in an electrochemical method for monitoring of a select analyte in a mixed sample with an interfering analyte, an improvement is provided that includes applying a large amplitude potential stimulus waveform to the sample to generate a nonlinear current signal; and resolving a signal contribution from the select analyte in the generated signal by a vector projection method with an analyte vector comprising a plurality of real and imaginary parts of one or more Fourier coefficients at one or more frequencies of a reference current signal for the select analyte.

According to another illustrative embodiment, an electrochemical method of determining concentration of a select analyte in a mixed sample with an interfering analyte is provided that includes applying a large amplitude potential stimulus waveform to the sample to generate a nonlinear current signal; measuring the generated signal; computing at least one parameter of all or some portion of the generated signal; and determining a concentration of the select analyte in the mixed sample by resolving an estimation equation based on analyte vectors for each of the select and interfering analytes and the at least one parameter.

According to another illustrative embodiment, an apparatus is provided that includes a potentiostat circuit for applying a voltage waveform to and detecting a resulting current from an electrode system; at least one memory having program instructions and a processor configured to execute the program instructions to perform the operations of: applying a large amplitude potential stimulus waveform to the sample to generate a nonlinear current signal; measuring the generated signal; computing at least one Fourier coefficient of a desired frequency component of all or some portion of the generated signal; and determining a concentration of the select analyte in the mixed sample by use of the at least one Fourier coefficient to resolve an estimation equation based on analyte vectors for each of the select and interfering analytes.

According to another illustrative embodiment, a method of constructing an estimation equation for monitoring a select analyte in a mixed sample with an interfering analyte is provided that includes selecting a large amplitude potential stimulus waveform to generate a nonlinear current signal when applied to the sample; applying the waveform to samples containing multiple different concentrations of each of the select and interfering analytes alone, and measuring the resulting reference current signals; computing values of real and imaginary parts of a Fourier transform for each of the reference current signals; plotting the real and imaginary values of a Fourier coefficient of the Fourier transform at each of a multiple number of frequencies; selecting one of the multiple frequencies at which the real and imaginary parts exhibit a relatively larger difference in phase angle; computing analyte vectors for each of the select and interfering analytes at the selected one frequency; and constructing the estimation equation based on the analyte vectors and calibration information that relates a concentration of the respective analyte in the sample to a length of the respective analyte vector in a complex plane.

According to another illustrative embodiment, a method of constructing an estimation equation for monitoring a select analyte in a mixed sample with an interfering analyte is provided that includes: selecting a large amplitude potential stimulus waveform to generate a nonlinear current signal when applied to the sample; selecting signal features of the current signal to use as parameters; applying the waveform to samples containing different concentrations of both the select and interfering analytes, and measuring the resulting reference current signals; computing values of each parameter for each reference signal; constructing the estimation equation as a linear estimator, having a select number of the parameters, from the computed values and with sufficient accuracy to estimate a concentration of the select analyte in the samples.

According to another illustrative embodiment, an electrochemical method of determining concentration of a select analyte in a mixed sample with an interfering analyte is provided that includes: applying a stimulus waveform to the sample to generate a nonlinear signal; measuring the generated signal; computing at least one parameter of all or some portion of the generated signal; and determining a concentration of the select analyte in the mixed sample by resolving an estimation equation based on analyte vectors for each of the select and interfering analytes and the at least one parameter.

According to another illustrative embodiment, a method for determining concentration of analytes in a mixed sample with an interfering analyte is provided that includes: applying a stimulus waveform to the sample to generate a nonlinear signal; measuring the generated signal; computing at least one parameter of all or some portion of the generated signal; and determining a concentration of the analytes in the mixed sample by resolving an estimation equation based on analyte vectors for each of the analytes and the at least one parameter.

It is to be understood that both the foregoing summary and the following detailed description are exemplary and explanatory only and are not restrictive to the invention as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 15 is table showing an example of typical reference readings that could be taken to provide test data for the method of FIG. 14;

DETAILED DESCRIPTION

Reference will now be made in detail to several illustrative embodiments of the present invention, examples of which are shown in the accompanying drawings. Wherever possible, the same reference numbers will be used throughout the drawings to refer to the same or like parts.

Systems and methods are provided herein for improving the selectivity and productivity of sensors via digital signal processing techniques. In particular, in accordance with certain illustrative embodiments, methods are provided herein for differentiating between electrochemical signal sources (ESSs), e.g., analytes, to resolve and preferably quantify the signal contribution from a select ESS to a total measured signal. In this way, the interfering contribution of an overlapping analyte such as ascorbic acid can be substantially reduced to more accurately measure the quantity of a target analyte, such as glucose.

Figure 5:
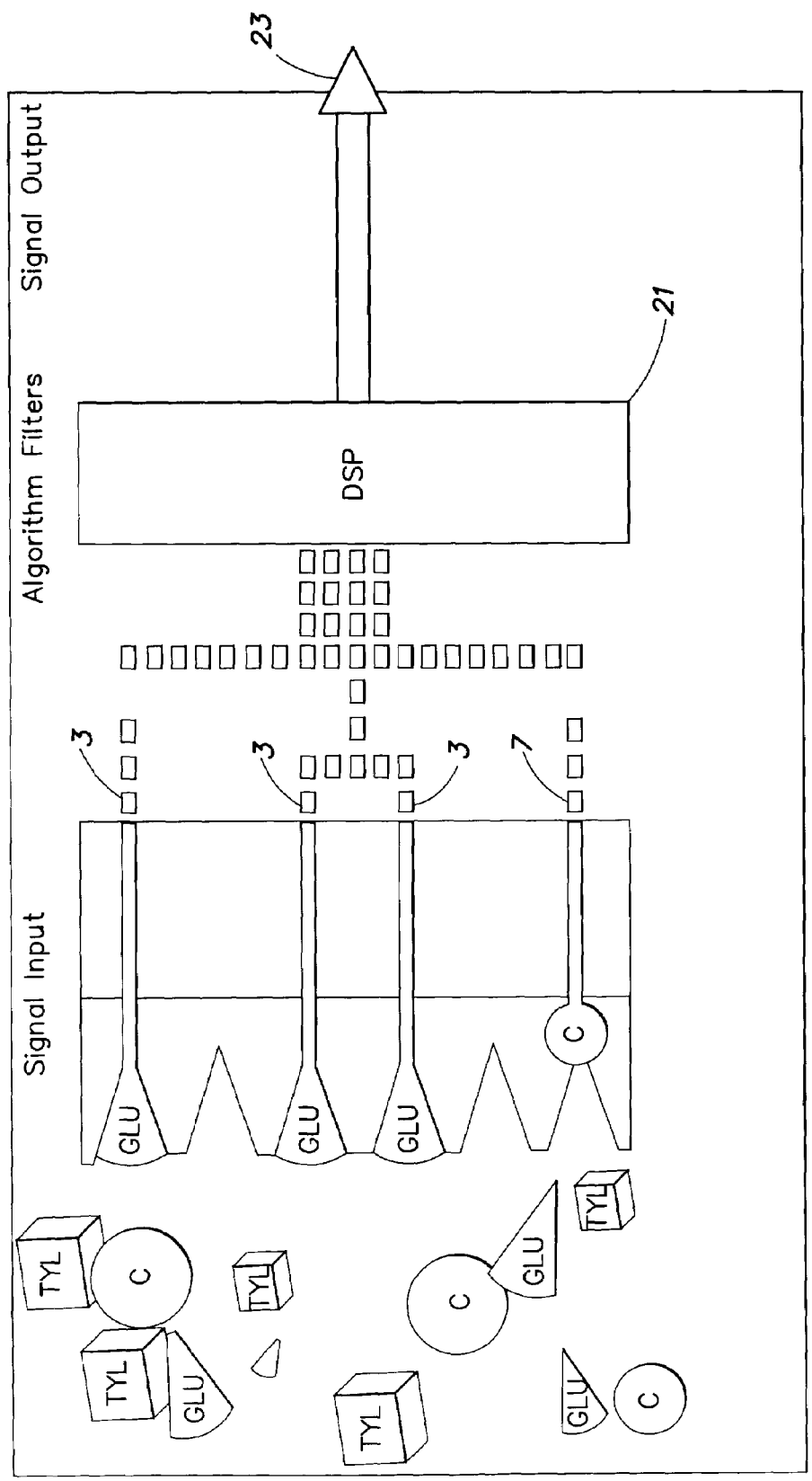
FIG. 5 is a biosensor for sensing glucose in a sample that utilizes digital signal processing to filter out the interfering effects-of ascorbic acid in accordance with an illustrative embodiment.
Figure 6A:
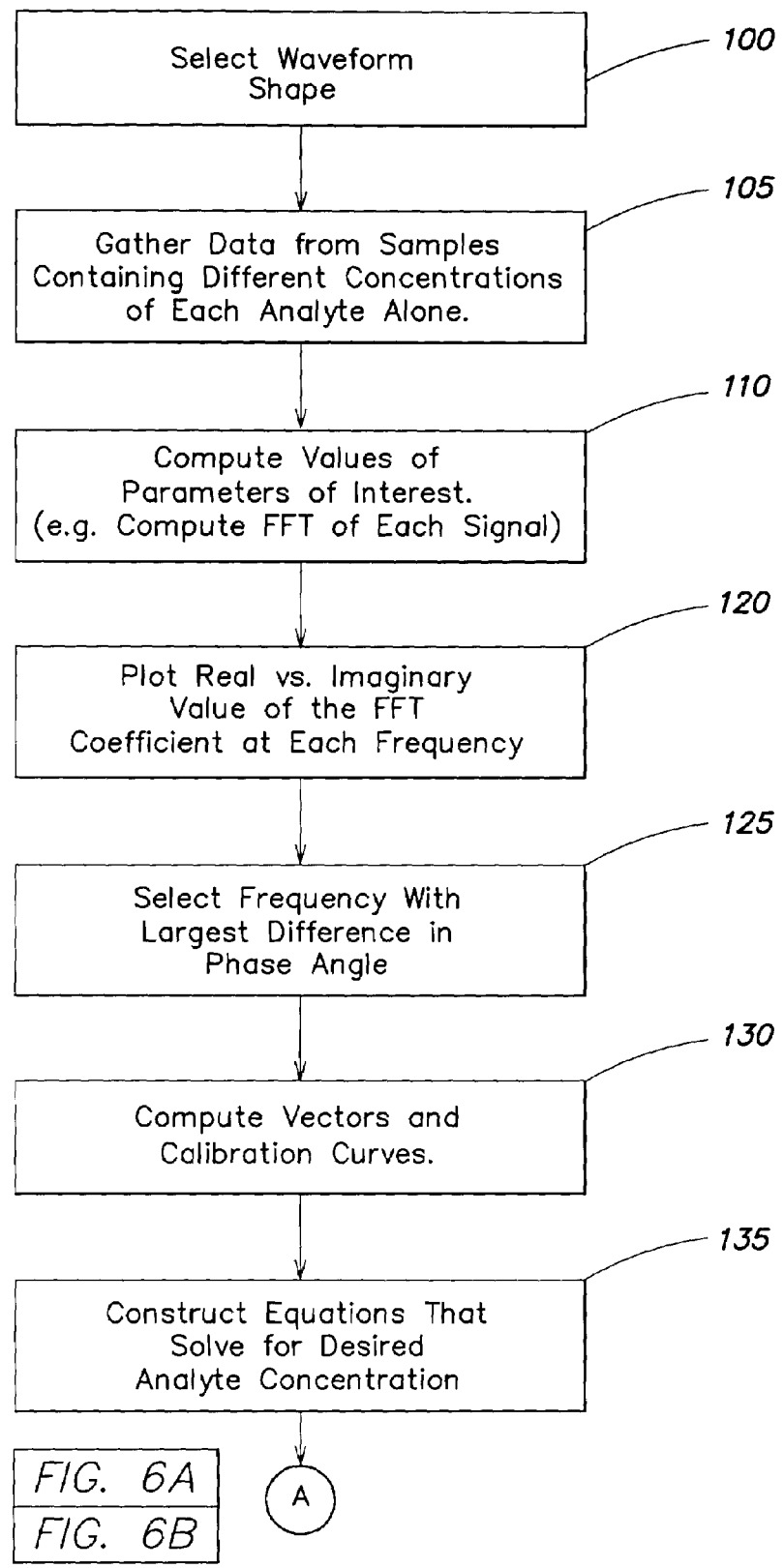
FIG. 6 is flow diagram illustrating a method for processing biosensor signals in accordance with another illustrative embodiment.
Figure 6B:
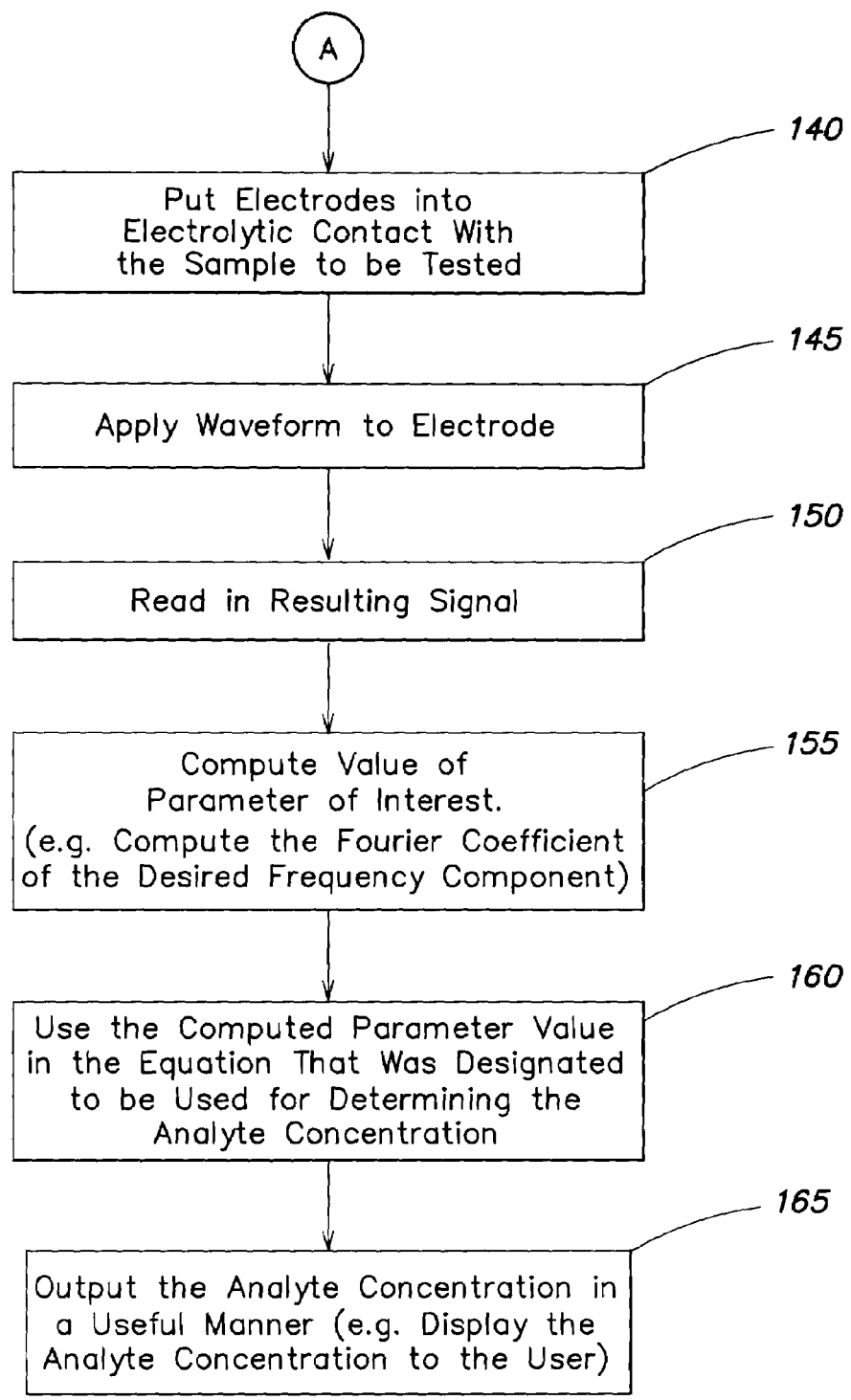
Figure 7:
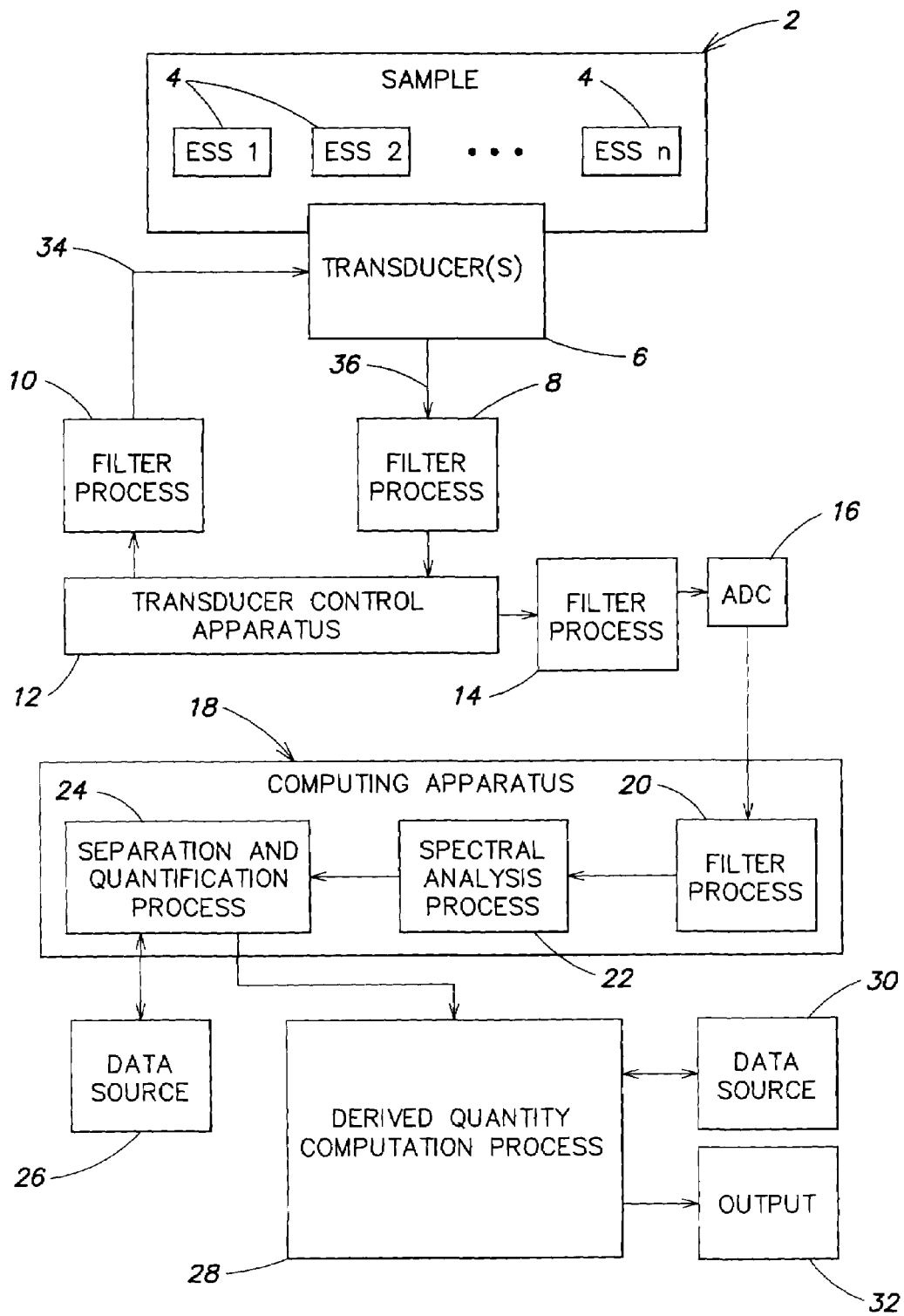
FIG. 7 is a system for processing biosensor signals in accordance with another illustrative embodiment.

FIGS. 5–7 show one illustrative embodiment of a method and system for determining the signal contributions of one or more analytes that generate an electrochemical signal in response to an applied voltage waveform. The relative signal contributions are then compared to the total measured signal to determine the concentration of one or more analytes. FIG. 6 illustrates the method in flow diagram form.

Figure 1:
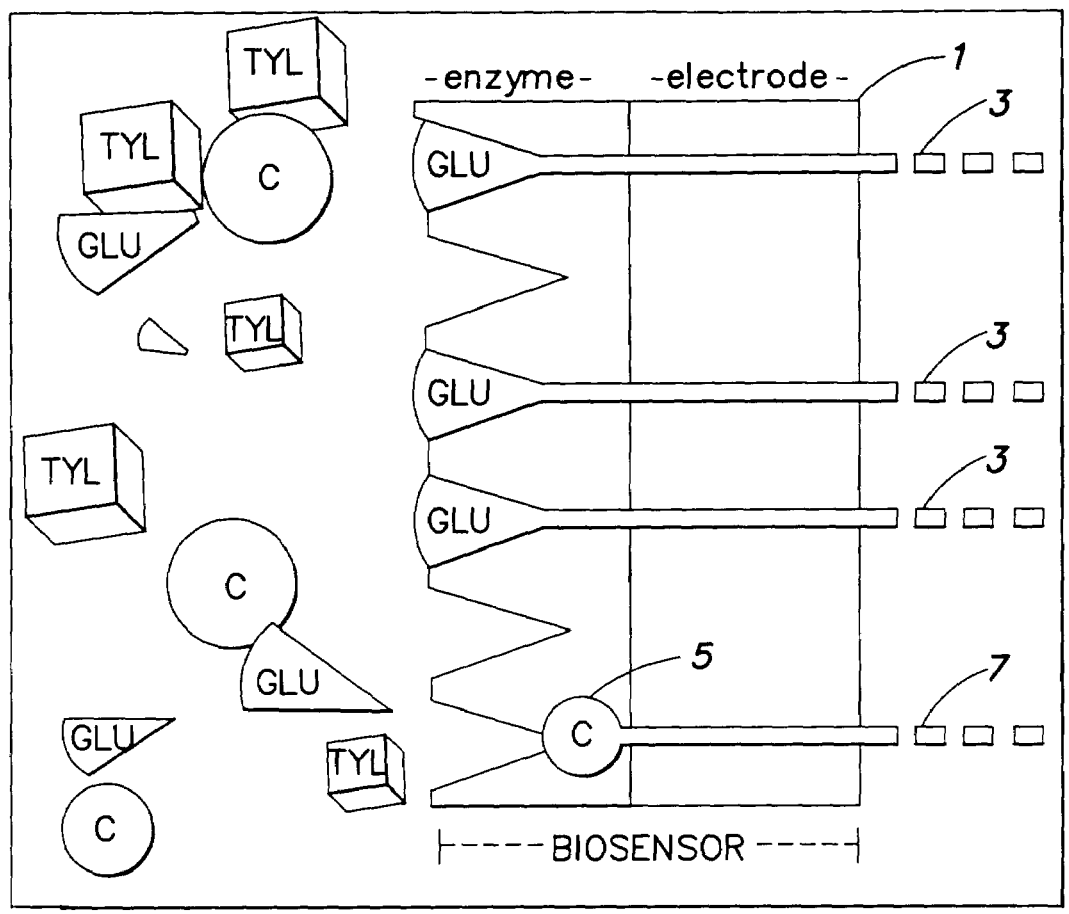
FIG. 1 is a biosensor for sensing glucose in a sample.
Figure 2:
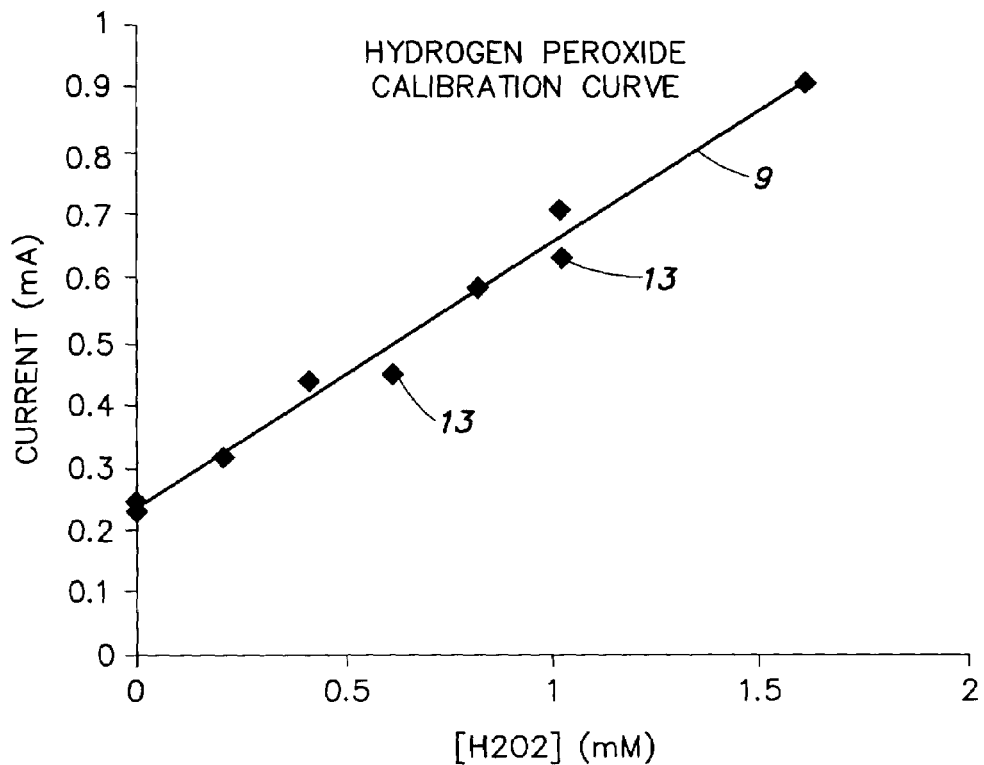
FIG. 2 is calibration curve showing the increase in current due to increasing amounts of hydrogen peroxide.
Figure 3:
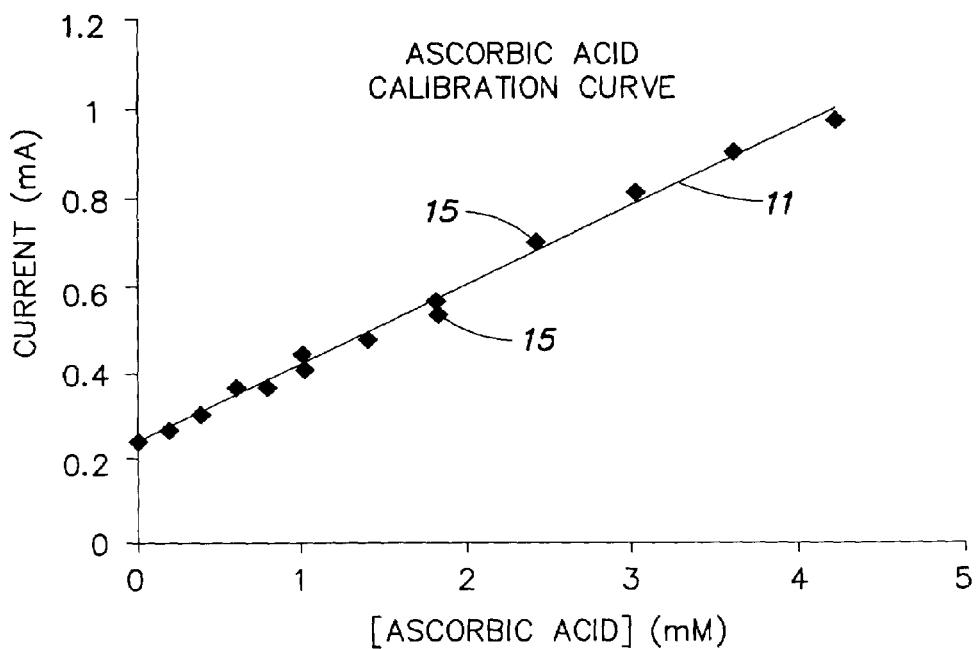
FIG. 3 is calibration curve showing the increase in current due to increasing amounts of ascorbic acid.
Figure 4:
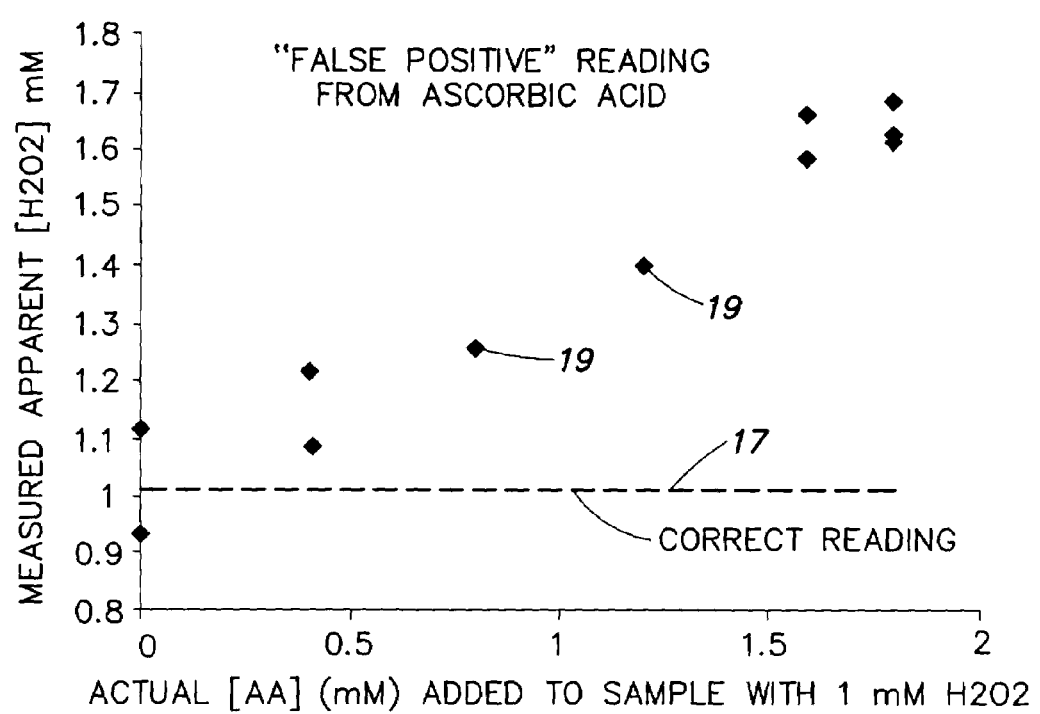
FIG. 4 is a chart illustrating false biosensor readings that can result from increasing amounts of ascorbic acid.

As shown in FIG. 5, the method could be implemented by adding digital signal processing hardware, firmware, or software 17 to the biosensor of FIG. 1. In this embodiment, DSP 17 performs mathematical operations on the measured signal to mathematically filter out some or essentially all of the current signal 7 generated from interfering analyte ascorbic acid and allows the contribution from the desired analyte signal 3 to be quantified; thus permitting the signal output 19 to be used to calculate the concentration of glucose in the sample. FIG. 7 shows a more detailed example of a system for carrying out the method of FIG. 6, but it should be understood that the method of FIG. 6 could be implemented by any number of different systems and apparatus. The system of FIG. 7 could in turn be implemented as a handheld tester, for example, for testing glucose concentrations in blood.

Referring to FIG. 6, a waveform shape is selected (step 100) to be applied to samples containing known concentrations of each analyte by itself (without other analytes that also give rise to interfering signals) to gather reference data (step 105). In this example, the waveform is used to gather data from samples that contain different concentrations of hydrogen peroxide in buffer without ascorbic acid, and then the waveform is used to gather data from samples that contain different concentrations of ascorbic acid in buffer without hydrogen peroxide. This same waveform is applied to the sample containing a mixture of unknown concentrations of both analytes. In this example, hydrogen peroxide is identified as the desired (or target) analyte and ascorbic acid is identified to be the interfering analyte.

Preferably, the stimulus waveform is a large amplitude waveform. The phrase "large amplitude waveform," as used herein, denotes a waveform (typically above 50 mV of variation) that will generate a nonlinear signal response from the sample. The waveform can be selected through a combination of experimental trials and theoretical consideration of the processes that are involved in the detection process. The selection of the waveform is done via a combination of theoretical and experimental considerations in order to achieve certain unique signal characteristics generated by a particular analyte. The factors generally recognized to affect an analyte signal are reaction rate and mechanism, generally referred to as the kinetics of the reaction, and the transport properties of the analyte.

The rate of the reaction kinetics or transport properties can influence the selection of the shape of the stimulus waveform. For example, reactions with fast kinetics or transport properties can generally reestablish equilibrium quickly in response to a voltage perturbation. Thus, if one wishes to probe analytes with fast processes one could select a voltage that varies quickly. Alternatively, some analytes have slow kinetics or transport properties and may take longer to reestablish equilibrium. Thus one could probe these with voltage waveforms that vary more slowly.

Factors to keep in mind when choosing a waveform include but are not limited to: the use of more positive potentials of the working electrode with respect to the reference electrode will generally increase the rate of oxidation; similarly, use of more negative potentials of the working electrode with respect to the reference electrode will generally increase the rate of reduction; and when the rate of kinetics is much faster than the rate of transport of the analyte (usually by diffusion), further increasing the rate of kinetics by increasing the potential in the appropriate direction (positive for oxidations or negative for reductions) generally will not significantly increase the current flow.

Figure 8:
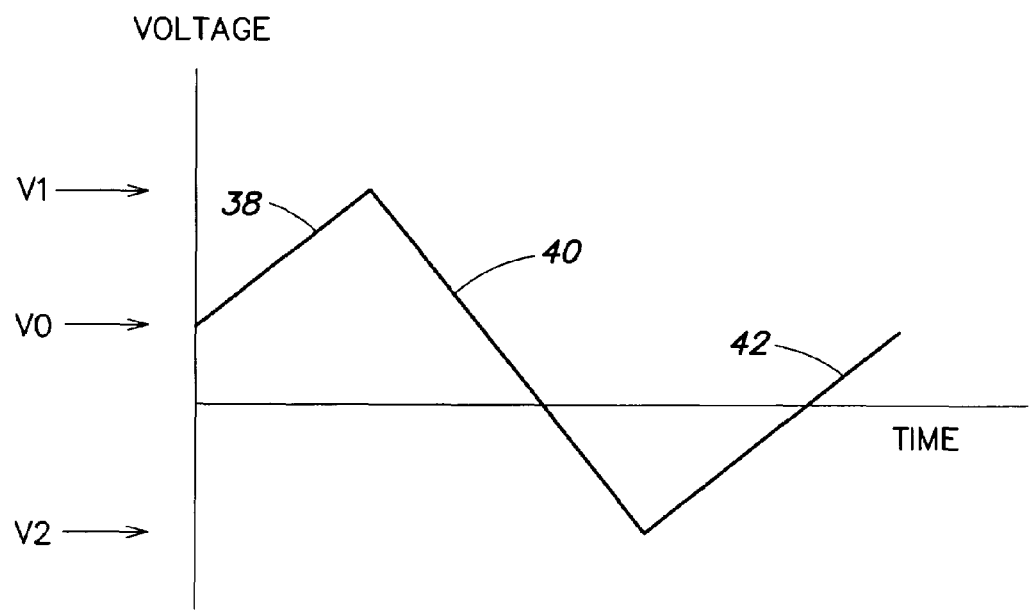
FIG. 8 shows the format for a waveform to be applied to a sample in accordance with an illustrative embodiment.
Figure 9:
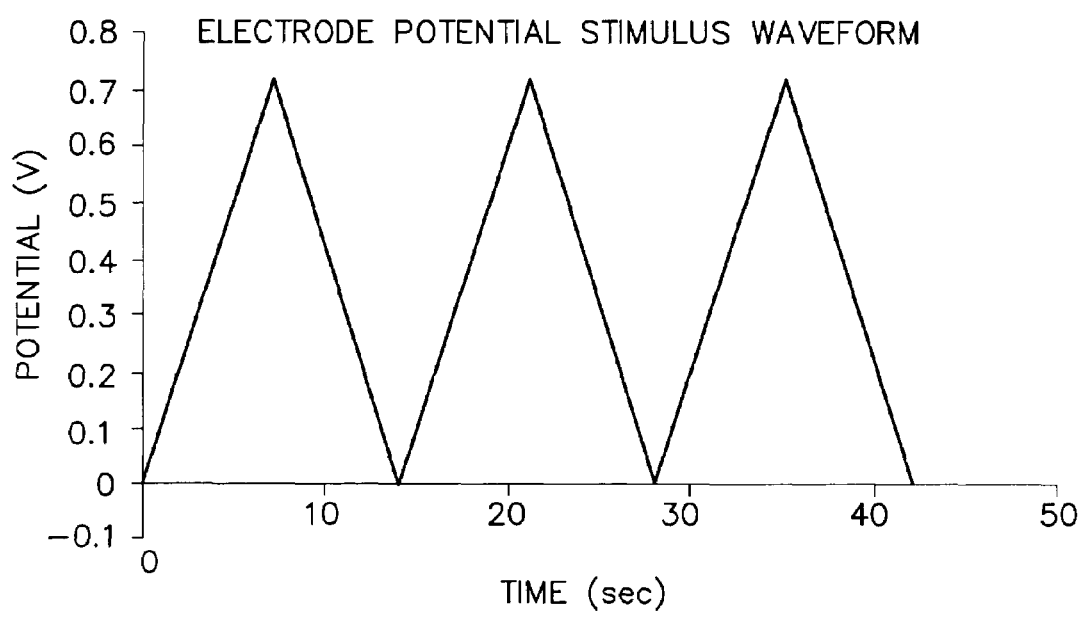
FIG. 9 shows a waveform applied to sample in accordance with an illustrative example performed using the method of FIG. 6.

A typical waveform format is shown in FIG. 8. The rates of change 38 and 42 are the same with the rate of change 40 being equal and opposite. The absolute value of V1–V2 is usually greater than 100 mV, though not necessarily so for all applications. In the example described in detail below, an appropriate waveform for glucose monitoring is shown in FIG. 9.

After selecting the waveform, data is gathered from samples containing different concentrations of the target and interfering analytes by themselves (step 105). For example, in distinguishing and determining the concentrations of peroxide and ascorbic acid one could make five repeated measurements using the selected waveform for each of the following concentrations for peroxide: 0 mM, 0.1 mM, 0.2 mM, 0.3 mM, 0.5 mM, 1.0 mM, 2.5 mM, 3.0 mM, 3.5 mM, 4.0 mM, 4.5 mM, 5.0 mM; and also five repeated measurements for the same ascorbic acid concentrations.

A set of parameters (one or more parameters), from the resultant current is then computed from each measurement (step 110). The selected parameter set reveals a relatively unique and measurable characteristic of the each analyte. A parameter may be any feature of the signal, or any function of any portion (or all) of the signal. Examples of parameters include frequency-domain items such as Fourier transform coefficients at various frequencies. Other examples of parameters include time-domain features such as, but not limited to, the slope of the signal at a particular point of the signal, the rise or decay rate of some portion of the signal, the average value of some portion of the signal, the value of the signal at some point in time, the voltage that is required to produce a peak or a valley in the signal, etc. In this illustrative embodiment, the values of the Fourier coefficients as computed by a FFT (fast Fourier transform) are the parameters that have been designated to be of interest. Thus, the FFT of each signal that was measured is computed and the FFT coefficients stored in computer memory.

In steps 120 and 125 the frequency is selected that gives the best resolution of the FFT coefficients between the analytes. This is done by plotting the real vs. imaginary value of the FFT coefficient at each frequency (step 120). Thus a series of plots is created that has the real value of FFT coefficient on one axis and the imaginary value of the FFT coefficient on the other axis. Thus, if 128 frequencies are being considered, 128 different plots are constructed, one for each frequency.

Each plot graphically shows the FFT value (real versus imaginary) at one frequency for all the data points (corresponding to different concentrations of each analyte). The plots are screened to determine which frequency corresponds to the relatively greater separation between the two analyte vectors (step 125). This can be referred to as the "angle separation" (angle or phase angle separation) between the analyte vectors. The phrase "analyte vector," as, used herein, denotes a vector of any length (although commonly of length one) which has a direction that is parallel to the direction of increasing analyte concentration when considered in a multidimensional space—each dimension of the space corresponding to a particular parameter being measured. The angle between the analyte vectors can be computed using a linear algebra technique known as vector dot product, or can be done simply by inspection of the plots.

Additionally, factors other than degree of separation can be considered when selecting the frequency. For example, the scatter on the data points should be considered. A well-separated set of vectors may not be as desirable if the noise from the scatter is very large. The sensitivity of the signal to the analyte concentration may also be considered. For example, the vectors may be well-separated, but the analyte signal may be weak. Thus, it may take 10 mM of the analyte to generate 1 unit of signal at that particular frequency, whereas if another frequency (or set of parameters) were selected where the vector separation may be less, the signal may be significantly stronger (e.g., 10 mM of the analyte gives 100 units of signal). Thus, we may choose a less separated vector parameter if it affords other benefits such as this.

Figure 10:
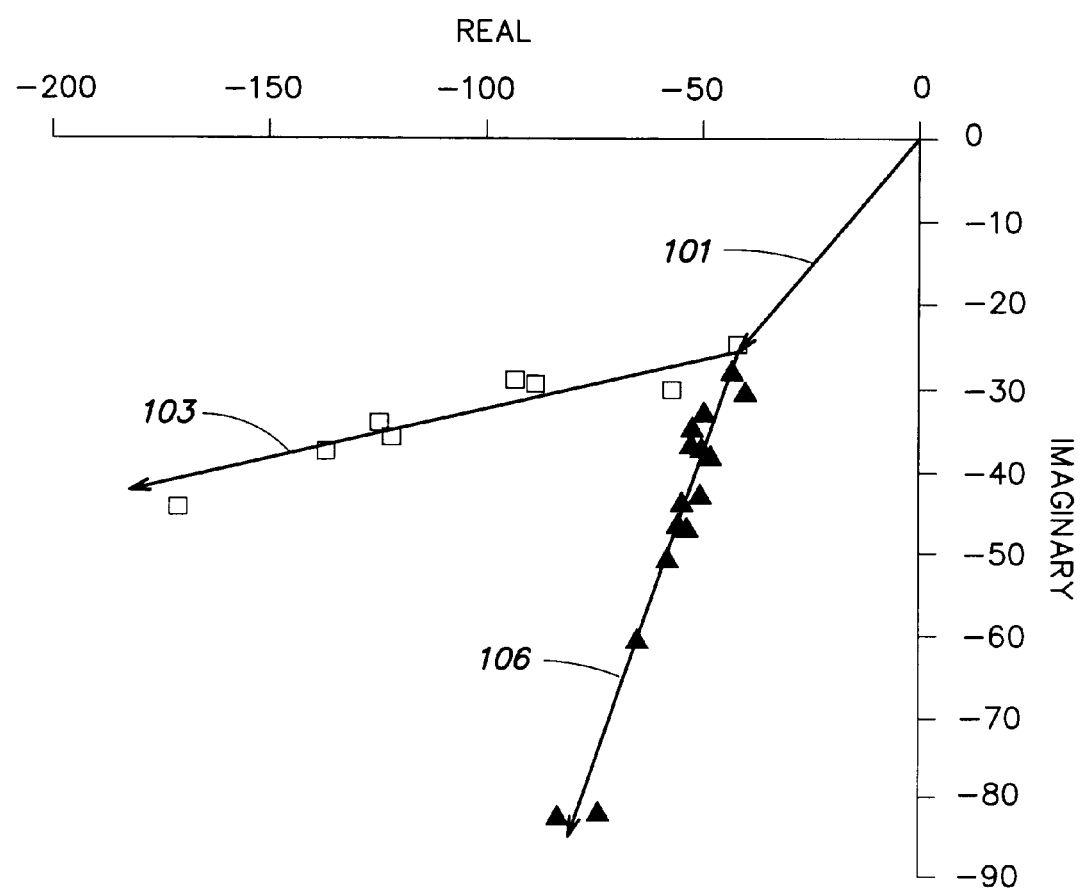
FIG. 10 is a chart showing the complex Fourier coefficients at a particular frequency in samples that contain only hydrogen peroxide or only ascorbic acid in the illustrative example.

Next, in step 130, at the selected frequency which gives the select angle separation, the following mathematical quantities are computed: values of each unit vector that lie in the same direction as each analyte vector (that is, determine the vectors of length one that have the same direction as each of the analyte vectors 103 and 106 in FIG. 10; values of the calibration curves that relate to the concentration of the analyte to the length of the vector in the complex plane; and the value of the "blank" buffer signal vector. The blank buffer signal vector represents the signal that is measured in the absence of both analytes. Thus, the blank buffer signal may be thought of as the baseline or background signal that exists when no analytes are present (although it should be noted that other constants may be used as the baseline signal in the estimation equations discussed below). In step 135, the values computed in step 130 are used to construct equations used to determine the target analyte concentration.

Samples containing unknown concentrations of the target and interfering analyte can now be measured. In step 140, electrodes are put into electrolytic contact with the sample to be tested. The same waveform selected in step 100 is applied to the working electrode (step 145). Under certain circumstances, it might also be desirable to apply the waveform prior to putting the electrodes in electrolytic contact with the sample. For example, it may be helpful to detect the time when the sample first comes into contact with the electrodes, for example, if there are very fast reactions that need to be monitored and the exact starting point of the reaction needs to be known.

In step 155, the fast Fourier transform is taken of all or a portion of the measured signal and the Fourier coefficients are computed at the same frequency selected in step 125. This value, a complex number, is used in the equation determined in step 135 to calculate the concentration of the desired analyte. The particular analyte concentration is then output in any useful manner, for example, displayed on an LCD (step 165); alternatively, it can be simply stored and/or used in a subsequent process.

FIG. 7 shows a system to implement the method of FIG. 6. Such a system could, for example, be implemented as a handheld tester, such as a tester used to detect glucose concentration in blood. The system includes transducer 6 for detecting electrochemical signals sources (ESSs) 4 generated by independent analytes in a sample 2. Transducer 6 is, for example, an enzyme-coated electrode as shown in FIG. 1 that is placed in electrolytic contact with sample 2. Other examples of transducers include but are not limited to electrodes with membranes, chemically modified electrodes, or other elements that can be used as electrochemical transducers.

A control signal 34 is applied to the transducer from transducer control apparatus 12 via filter process 10 (see step 145). A time domain signal 36 is generated at transducers 6, is filtered by filter process 8, and stored in transducer control apparatus 12 (see step 150). The transducer control apparatus 12 measures the applied potential 34 and the measured current 36 as a function of time.

The signal is again filtered by filter process 14 which may be, for example, an anti-aliasing filter, a high pass filter, a low pass filter, a band pass filter, and/or a band stop filter. The signal is then converted from analog to digital form to enable digital processing of the signal by computing apparatus 18, using an analog to digital converter 16. The digital computing apparatus can be, for example, a digital signal processor chip but may also include analog circuits, digital circuits, microprocessors, and/or optical computing apparatus. Furthermore, although preferably digital signal processing is performed on the signal 36 the foregoing processing can also be performed by an equivalent analog circuit.

Computing apparatus includes a filter process 20 that filters the signal in order to reshape it and/or transform the signal to a more optimal wave form better suited for digital processing. The filter process 20 can be used to enhance and/or suppress different spectral components in the signal. For example, the filtering process can be used to smooth the signal to reduce high, mid, and/or low frequency variations as well as alter the spectral properties of the signal including changing the phase angle spectrum and the magnitude spectrum. A spectral analysis process 22 is then performed on all or a portion of the signal which is commonly done using a mathematical technique such as fast Fourier transform which generates the magnitude and phase angle of each frequency component of the signal (see step 155).

A separation and quantification process 24 is then performed on the spectral content of the signal processed by 22 (see step 160). Process 24 uses a set of equations constructed based on the known spectral characteristics of each ESS from data source 26 (see step 135). Data source 26 may include for example equations that describe how each ESS interacts with other ESSs in the sample, data about the known spectral characteristics of each ESS that may be gathered by electrochemical assay of each ESS, and/or equations that describe how each ESS generates the signal that is measured by the transducers. Thus, using data source 26, separation and quantification process 24 solves a set of equations to find a solution that quantifies the signal contribution from each ESS of the total measured signal (see step 160).

For example, once both potential and current signals have been acquired by the computing apparatus 18 a reference point in time is taken. Commonly this reference point is taken with respect to potential signal 34, which is the independent variable, and current signal 36 is the dependent variable. For example, when employing cycle voltammetry such a reference point may be taken as the time at which the applied potential reaches a value of V1, as illustrated in FIG. 8. Both current and potential values are recorded as a function of time relative to the reference point in time (step 150). The frequency spectrum is then computed for the current signal by spectral analysis process 22. This may be accomplished by a variety of methods but the most common method is to compute the Fourier transform via a fast Fourier transform, discrete Fourier transform or other similar method (step 155).

Computing the spectrum of the current signal gives at least the following two results: the phase angle spectrum and the magnitude spectrum. The phase angle spectrum will be independent of the strength of the signal contribution from an ESS but the magnitude spectrum will be a function of the strength of the signal of the contribution from an ESS. For example, it is commonly observed that the magnitude spectrum will depend on the concentration of the electroactive chemical species as present in the sample and that the phase angle spectrum does not vary with concentration.

The spectral features from spectral analysis 22 are used by separation and quantification process 24 to resolve and separate the components of the measured current signal that arise from the different ESSs 4 and quantify the contribution of each ESS 4 to the total measured signal 36. One example of how these features may be used is that the phase angle spectrum from each ESS may be used as its signal "fingerprint" that is unique to that particular ESS in order to identify and resolve the signal from that particular ESS from the other signal components of other ESSs, and the magnitude spectrum may be used to quantify the amount of that signal present. The information about the phase angle spectrum of an ESS may be from a data source 26 and may include but is not limited to spectral analysis data from the analysis of samples that contain only one ESS (see steps 105–135).

The quantification of the signal strength from an ESS can then be used by a derived quantity computation process 28 to calculate derived quantities by using other relevant data from a data source 30. One example of derived data includes but is not limited to calculating the concentration of the target analyte in the sample by comparison to calibration data, e.g., calibration curves for the target analyte (see step 130). The output 32 can then be given in usable format which may include an LCD readout (see step 165).

EXAMPLE 1

An example of the method of FIG. 6 and system as carried out by, for example, a system of FIG. 7, is now described in terms of analyzing the concentration of a sample containing peroxide and ascorbic acid. A 700 mV potential stimulus waveform shown in FIG. 9 was used (step 100). The scan rate of the stimulus waveform was 100 mV per second in both the upscan and downscan directions. The resulting current was sampled in time at a sampling frequency of 40 hz. The spectral content of the current signal was computed with the fast Fourier transform (step 110).

FIG. 10 shows the complex Fourier coefficients for 0.4506 hz, which had the best separation between the analyte vectors. The open squares represent measurements made with the sample that contained peroxide and no ascorbic acid. The black triangles represent measurements made with a sample that contained ascorbic acid and no peroxide. (See steps 105–120). Vector 101 represents the baseline background signal ($\vec{Y}_{blank}$); analyte vector 103 is in the same direction as the unit vector that represents the direction that increasing concentrations of peroxide move along ($\vec{i}_{HP}$); analyte vector 106 is in the same direction as the unit vector that represents the direction that increasing amounts of ascorbic acid move ($\vec{i}_{AA}$) Thus, it can be seen that the peroxide signal only manifests itself in one direction in the complex plane and the ascorbic acid signal only manifests itself along a different direction in the complex plane. In this case, the following equations are obtained:

$$\vec{Y}_{blank} = -41.2 - j27.7$$

$$\vec{i}_{HP} = 0.995 - j0.101$$

$$\vec{i}_{AA} = 0.591 - j0.807,$$

where $\vec{i}_{HP}$ and $\vec{i}_{AA}$ are vectors of a unit length.

Figure 11A:
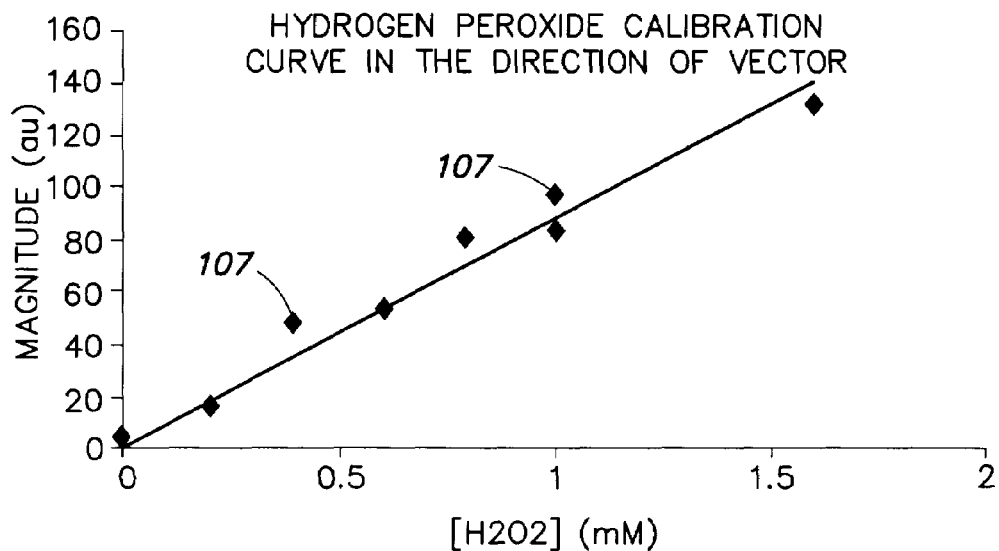
FIGS. 11($a$) and ($b$) show calibration curves for hydrogen peroxide and ascorbic acid, respectively.
Figure 11B:
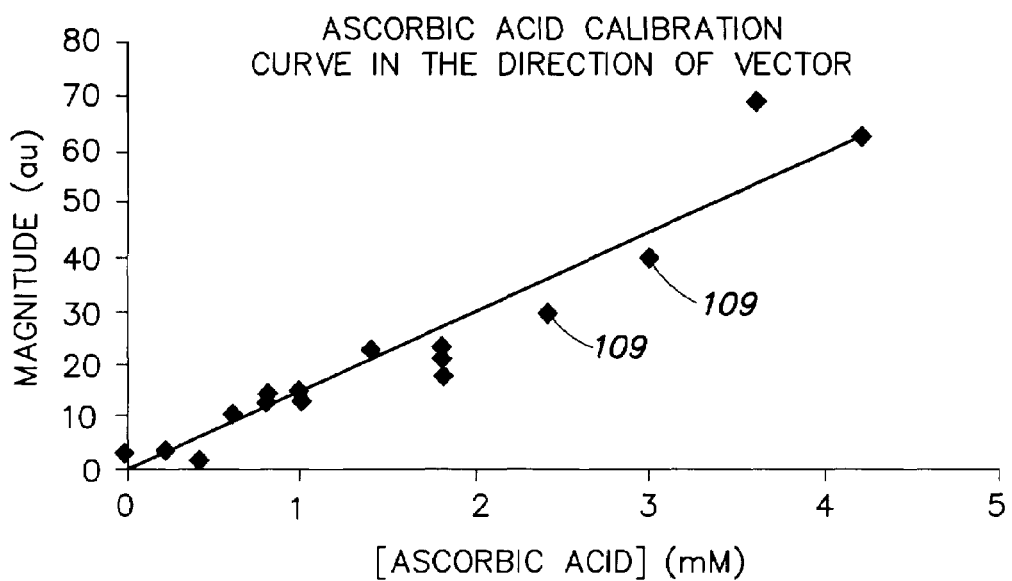

Calibration curves are then constructed (step 130). FIGS. 11a and 11b show the calibration curves of peroxide and ascorbic acid, respectively, in the direction of the characteristic unit vector taken with respect to the experimental origin. The experimental origin is given by $\vec{Y}_{blank}$. That is, the magnitude of the signal is computed by subtracting $\vec{Y}_{blank}$ from each of the complex data points (107 and 109) and then computing the Euclidean distance from the origin given by (0,0). The magnitude is represented in arbitrary units (au) that are proportional to the current signal; however, due to the nature of computing FFT coefficients, the actual magnitude can be a scalar multiple of the current, as determined by the number of samples used in the FFT. Thus, for the sake of generality, magnitudes of the FFT are given in arbitrary units.

The calibration equations are given by:

$$I_{H2O2} = 87.89 * [H2O2] \text{ or}$$

$$[H2O2] = I_{H2O2}/87.89$$

And $$I_{AA} = 14.949 * [AA] \text{ or}$$

$$[AA] = I_{AA}/14.949$$

Where I is the signal magnitude given in au, and concentrations are in mM. The calibration curve coefficients can be combined with the vector information after the separation of the two signals is performed. Thus, let:

$$\vec{Y}_{HP} = \vec{i}_{HP} = (0.995 - j0.101)$$

$$\vec{Y}_{AA} = \vec{i}_{AA} = (0.591 - j0.807)$$

From vector relationships, the following are obtained:

$$\vec{Y}_{total} = a\vec{Y}_{HP} + b\vec{Y}_{AA} + \vec{Y}_{blank}$$

$$Y_{total\ r} = aY_{HP\ r} + bY_{AA\ r} + Y_{blank\ r}$$

$$Y_{total\ i} = aY_{HP\ i} + bY_{AA\ i} + Y_{blank\ i}$$

$$Y_{HP\ r} = (0.995)$$

$Y_{HP\ i} = (0.101)$ $Y_{AA\ r} = (0.591)$ $Y_{AA\ i} = (0.807)$ where $\vec{Y}_{total}$ is the FFT value that is obtained from some given sample. In this case, there are two unknowns (a and b) and two equations (step 135). Once a and b are solved, the resulting answer is the apparent measured signal magnitude for peroxide and ascorbic acid, respectively. Finally, this signal magnitude may be compared to the calibration curve equations to determine the desired concentrations (step 160):

$$a = \frac{-[(Y_{AAr})(Y_{blank\ i} - Y_{total\ i}) - (Y_{blank\ r} - Y_{total\ r})(Y_{AAi})]}{(Y_{HPi})(Y_{AAr}) - (Y_{HPr})(Y_{AAi})}$$

$$[H2O2] = \frac{a}{87.89}$$

$$b = \frac{-[(Y_{HPi})(Y_{blank\ r} - Y_{total\ r}) - (Y_{blank\ i} - Y_{total\ i})(Y_{HPr})]}{(Y_{HPi})(Y_{AAr}) - (Y_{HPr})(Y_{AAi})}$$

$$[AA] = \frac{b}{14.95}$$

Figure 12:
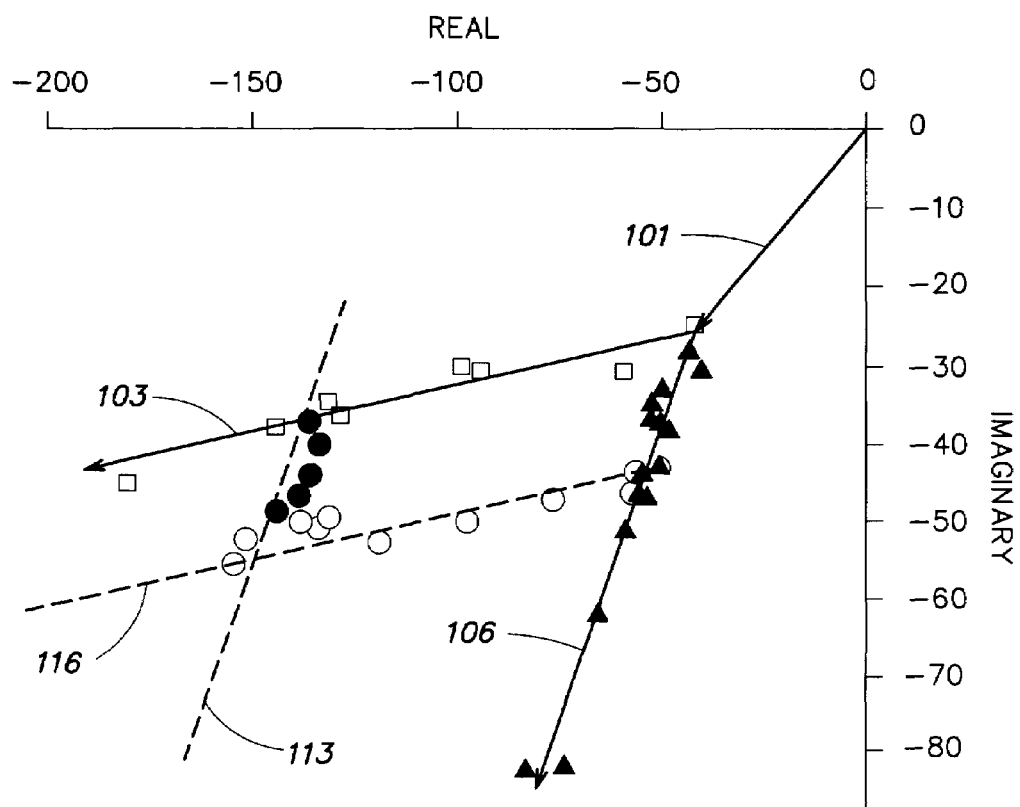
FIG. 12 is a chart showing the complex Fourier coefficients at a particular frequency in mixed sample of hydrogen peroxide and ascorbic acid in the illustrative example.

Accordingly, using these equations, the concentrations of peroxide and ascorbic acid can be determined in the given sample. Using these equations, several samples containing mixed amounts of peroxide and ascorbic acid were measured. FIG. 12 shows the data points that were gathered. Dashed line 116 shows measurements from a sample containing 1.8 mM ascorbic acid with increasing amounts of peroxide. The open circles represent the complex value of the FFT at this frequency and can be given by $\vec{Y}_{total}$. It is seen that as the concentration of peroxide is varied, the data points move along the same direction as given by $\vec{i}_{HP}$ 103, which is parallel to dashed line 116.

Dashed line 113 shows measurements from a sample containing 1.0 mM of peroxide with increasing amounts of ascorbic acid. The filled circles represent the complex value of the FFT at this frequency and can be given by $\vec{Y}_{total}$. It is seen that as the concentration of ascorbic acid is varied, the data points move along the same direction as given by $\vec{i}_{AA}$ 106, which is parallel to dashed line 113.

Thus, as stated above, the phase angle with respect to each analyte differs from one another and remains constant across differing samples. Vector 101 represents $\vec{Y}_{blank}$. Using the above equations, each of the data points measured in the mixed samples was used to determine the apparent [H2O2], which is ultimately the analyte of interest in this example.

Figure 13:
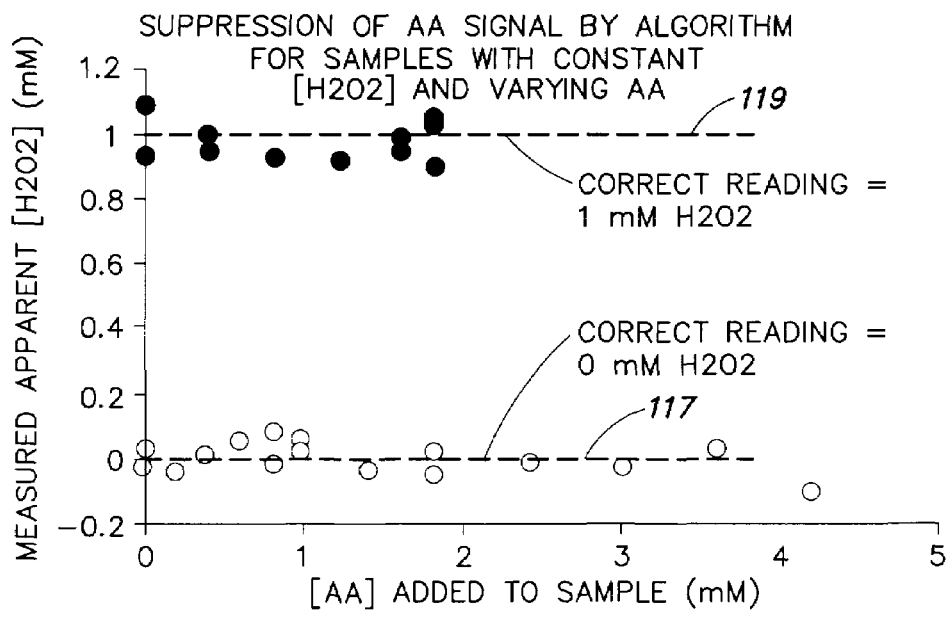
FIG. 13 is a chart showing the results of the illustrative example.

The results are shown in FIG. 13 in which two families of samples are illustrated. One family of samples has no peroxide, but varying amounts of ascorbic acid. For this set, the apparent [H2O2] should be close to 0 mM, as is correctly illustrated with dashed line 117. For the second family of samples, the concentration of peroxide was maintained at 1.0 mM, and varying amounts of ascorbic acid were added to the sample. In this case, the apparent [H2O2] should be close to 1 mM, as is again correctly illustrated with upper dashed line 119.

Thus, with the foregoing method, excellent resolution between the ascorbic acid signal and the peroxide signal is demonstrated thereby allowing for selective monitoring of peroxide in the presence of ascorbic acid, or vice versa.

In the foregoing illustrative embodiment shown in FIG. 6, one frequency of the fast Fourier transform is considered. In addition, only two parameters, the real and imaginary parts of that one frequency were considered together in determining separation in the angles of each of the analyte vectors (step 125). However, in accordance with a further illustrative embodiment, under certain circumstances greater separation and therefore better resolution between analytes may be achieved if more than the real and imaginary parts of just one frequency are considered, and more generally, if more than two parameters were used.

For example, one can consider the real part of 1 Hz versus the imaginary part of 4 Hz, or the real part of 3 Hz versus the real part of 12 Hz. Additionally, the space in which the unit vector is set can be expanded into higher dimensions since this can increase the separation between vectors. Thus, the real part of 2 Hz can be compared versus the imaginary part of 8 Hz versus the real part of 9 Hz. The angle between the data vectors is readily computed in the same way as it is in a two-dimensional space. Thus, the benefit of looking at higher dimensional parameters is that it gives more freedom to select the parameters that result in a greater separation of the analyte vectors.

Another reason for using more parameters is that one is able to pick and choose certain signal features that are highly correlated to the concentration of a particular analyte. For example, one may find that a slope of a particular section of the measured current signal is correlated to the concentration of a target analyte. It is likely that this signal feature might not get fully captured by any one FFT coefficient, so it may be desirable to compute the slope of the signal in the time domain as a separate parameter.

Figure 14B:
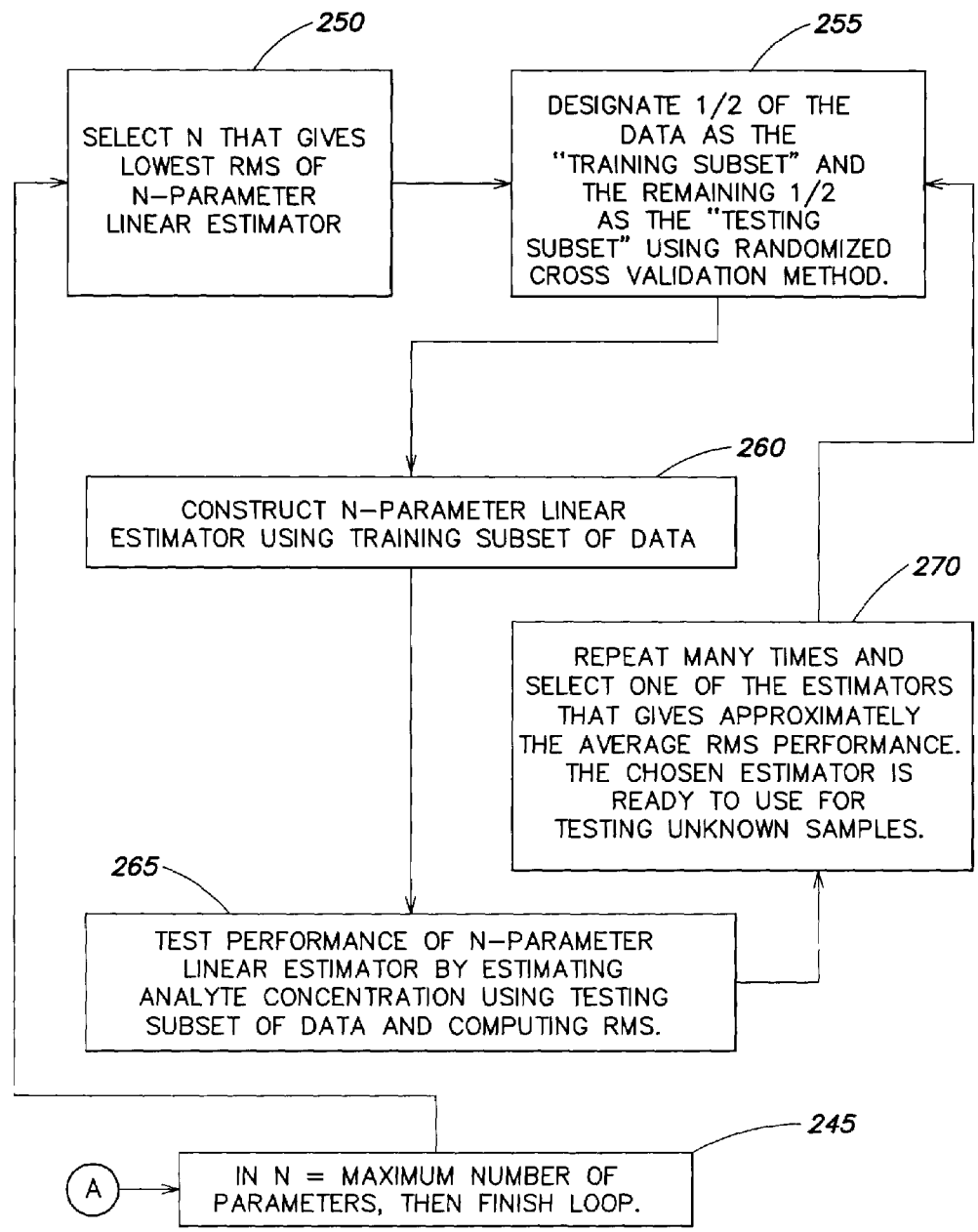
FIG. 14 is flow diagram illustrating a method for processing biosensor signals in accordance with another illustrative embodiment.

FIG. 14 illustrates a method for determining analyte concentrations using multiple parameters, i.e., more than one frequency and/or time-domain parameters. Step 200 is similar to step 100 described above in which a waveform to be applied to the sample is selected. Possible signal features are then determined which are used as parameters in the estimation algorithm described below (step 205). For example, the possible features to use as parameters include, but are not limited to, the Fourier coefficients (real or imaginary) at a particular frequency or frequencies as computed by the FFT; the Fourier coefficient, real or imaginary, of some portion of the signal (such as, for example, the tail end of the signal); the slope of the signal curve at some point in time; the rate of exponential rise or decay of some portion of the signal; the voltage at which a particular peak or valley of the signal occurs; the value of a particular peak or valley in the signal; etc.

Unlike the previous embodiment in which step 105 involved gathering data with respect to each analyte by itself, in step 210, data may be gathered from a matrix of different analyte concentrations that contain different concentrations of both analytes. For example, as shown in the matrix of FIG. 15, samples could be taken from each of the known concentrations of ascorbic acid and glucose resulting in a total of 130 different samples with each sample being used to gather five repetitions of data yielding a set of data with 650 recorded signals.

In step 215, values for each of the parameters of interest is computed for each signal in the data set, and are stored in memory. Steps 220 through 240 involve constructing a linear estimator. As shown in step 220, the method begins with a one parameter linear estimator. Thus, for the case where N=1, a randomized cross validation method is performed by using half of the data as a training subset and half of the data as the testing subset.

A randomized cross validation technique is a mathematical technique that is described in Gene H. Golub, Michael Heath and Grace Wabba, "*Generalized Cross Validation as a Method for Choosing a Good Ridge Parameter*", Technometrics 21, pp. 215–223 (1979). Using this method, an optimum number of parameters can be found for which the average RMS (root mean square) is lowest. As one constructs linear estimators with more and more parameters, the RMS error of the estimator would decrease to a certain minimum. Further increases in the number of parameters would worsen the performance of the estimators, thereby giving increasing RMS values. It should be noted that some measure of accuracy other than RMS could be used such as: adjusted RMS, variance, standard deviation, etc.

Starting with one parameter and increasing, the estimator is constructed (step 230) and its performance is determined by estimating analyte concentration using the testing subset of data and computing the RMS. When using the randomized cross validation method, one can start with any of the parameters, or a particular ordering of parameters can be specified when building estimators that use more and more parameters.

The general form of the linear estimator equation used is given by:

$$[Analyte(n)] = \sum_{k=1}^{N} h_k Y_k(n),$$

where:
[Analyte(n)] is the estimated analyte concentration for sample n;
$Y_k$ is a parameter, such as the real or imaginary part of an FFT coefficient at a particular frequency; and
$h_k$ is the associated weight for that parameter and may be thought of as a measure of the information content that the parameter holds.

Steps 225 through 240 determine the maximum number of parameters that may be used to gain estimator performance based on information content rather than merely dimensional advantage. Dimensional advantage occurs when there are too many parameters describing a set of collected data. One example includes the situation where there are 5 data points. A model consisting of 5 parameters can be made to intersect each of the 5 data points. This would result in an estimator that yields RMS=0 when tested against the same data set that was used to construct the estimator, giving an estimation equation that falsely appears to perform perfectly, but is in fact not a robust estimation equation. Thus, it is preferable to determine a maximum allowable number of parameters to achieve optimal performance while maintaining a desired level of robustness. In the method illustrated in FIG. 14, this is achieved by using a process of randomized cross validation analysis.

Each estimator is used to estimate the target analyte concentration of the testing data subset (step 235). Since the correct concentrations of the target analyte(s) are known in each of the samples in the testing subset, to test the estimator, the data signal already recorded is processed according to the equation given by the estimator.

The estimator will yield a number corresponding to the concentration of the analyte resulting from the test signal that was just processed. In other words, the estimator will estimate the concentration of the target analyte that was used to record the test data signal. To test the performance of the estimator, the error between the linear estimator and the known target analyte concentration is computed (step 235). One way to compute such errors is to compute the RMS error. The linear estimator is used to estimate the analyte concentrations of all the signals in the test data subset and subsequently calculate the RMS error associated with each data point. The RMS error associated with each N-parameter linear estimator is stored in memory.

The randomized cross validation method is repeated by selecting new data subsets as the training subset and the testing subset (step 240). The construction of the one-parameter linear estimator is repeated by training on a new data subset. Again, the RMS error is stored for each training subset for the linear estimator. This process is repeated many times, for example, 1000 times. The average of the RMS of the entire series is computed. This gives an indication of the general performance of the linear estimator constructed in step 230. As often is the case, one will achieve better or worse performance depending on the selection of the data subsets that are used for training or testing. Using the randomized cross validation method, one can minimize errors in determining performance of the estimator by testing the estimator against different random selections of data.

Once the one-parameter linear estimator's average performance is determined by computing the average RMS, a two-parameter linear estimator is constructed and evaluated. The second parameter is selected as described above. The randomized cross validation testing method is again used to determine the average RMS performance of a two-parameter linear estimator. (Steps 225–240.)

Once the two-parameter linear estimator's performance has been determined by computing the average RMS, the three-parameter linear estimator's performance is determined, and so forth, increasing to the N-parameter linear estimator. When all of the available parameters set forth in step 205 have been used, the loop is finished (step 245). Next, the number of parameters N is selected that corresponds to the estimator that yielded the lowest RMS (step 250).

The N-parameter estimator is constructed and reconstructed many times, e.g., 1000 times, each time tested with a different random selection of training and test data (steps 255–270). The estimator is then chosen that gives the desired RMS performance. Often, but not always, the estimator that gives the average performance is chosen, since it is representative of the performance of the estimator on that given data set. This estimator is ready to use for testing unknown samples. Alternatively, one could choose the N-parameter estimator that gives the best performance (as opposed to the average RMS performance).

Thus, unlike the embodiment of FIG. 6, the embodiment of FIG. 14 considers more parameters than just the real and imaginary components of the Fourier transform at a single frequency, thereby constructing an analogous vector system in multi-dimensional space. The embodiment of FIG. 6 relied on two dimensional space, where each dimension corresponded to one parameter. In that embodiment, one parameter was the real part of the Fourier transform and the second parameter was the imaginary part of the Fourier transform at one frequency.

The embodiment of FIG. 14 relies on a multidimensional parameter space where each dimension corresponds to the selected parameter in which: the optimal number of parameters are selected so as to achieve good performance while constructing a robust estimator that does not succumb to dimensional advantage; and greater weight can be given to those parameters that are information-rich and thereby correlate more closely to the target analyte signal. The relative importance of each of the dimensions in the parameter space is weighted such that those dimensions (or parameters) that have a greater information content contribute more heavily to the final estimate of the target analyte concentration.

Because the embodiment of FIG. 6 used two parameters, namely, the real and imaginary parts of the Fourier transform at one frequency, the weights of each parameter were computed directly based on the unit vectors describing the directions of each analyte signal, for example, the peroxide signal $\vec{Y}_{HP}$ and the ascorbic acid signal $\vec{Y}_{AA}$. That is, when the measurement $\vec{Y}_{total} = Y_{total\ r} + jY_{total\ i}$ was made, each of the real and the imaginary part of the Fourier transform of the measured signal at the selected frequency were weighted appropriately, multiplying each of $Y_{total\ r}$ and $Y_{total\ i}$ by a scalar weight as set forth above.

The use of a multi-dimensional linear estimator allows the weighting to be automatically calculated over the entire set of parameters without having to explicitly determine the directional vectors for each analyte.

Generally, both illustrative embodiments (FIG. 6 and FIG. 14) utilize what is referred to herein as a "vector projection method." This method includes: selecting one or more parameters, each of which is a feature of the signal from the sample or the stimulus waveform; determining the analyte vector for each analyte, either explicitly or implicitly; and constructing an estimation equation based on the relative magnitudes and directions of the analyte vectors and the parameters, which can be used to estimate the concentration of an analyte in the sample.

EXAMPLE 2

Figure 16:
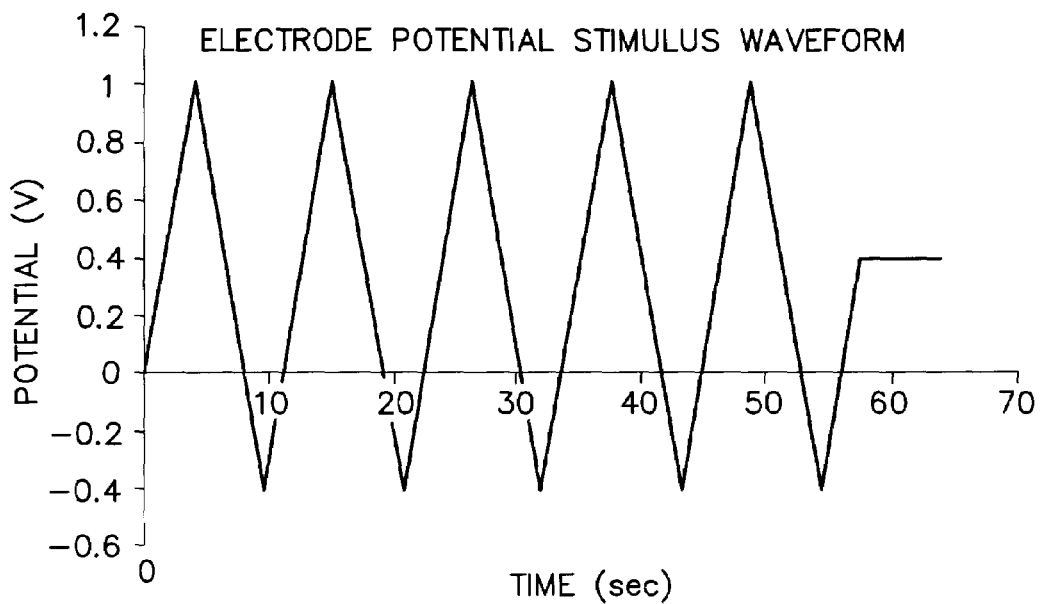
FIG. 16 shows a waveform applied to sample in accordance with a second illustrative example performed using the method of FIG. 14.

An example was performed using the method shown in FIG. 14. Glucose was the target analyte with ascorbic acid acting as the interferent, and blood as the sample matrix. The waveform shown in FIG. 16 was selected as the stimulus to be applied to the sample.

The waveform combines both cyclic voltammetry and DC amperometry. The potential is ramped in the upward direction at 250 mV/s, in the downward direction at −250 mV/s (the CV part of the signal), and is held constant at 0.4 V beginning at 57.6 seconds and ending at 64 seconds (DC amperometric part of the signal).

The "head" of the signal refers to the signal collected with this waveform between 0 seconds and 20.8 seconds, inclusive. In this case, the signal is sampled at 40 Hz, thereby providing 833 samples. The "tail" of the signal refers to the signal collected with this waveform between 61.475 seconds and 63.975 seconds, inclusive, giving 101 samples.

In this example, the following principles were observed.

Consider the measured current signal waveform in two separate sections: First, capture ascorbic acid dominated signal information from the head of the signal by computing the FFT and considering an appropriate combination of various real and imaginary parts of the Fourier transform value at different frequencies; and second, capture ascorbic acid and glucose combined information from the tail of the signal by computing the Fourier transform at 0 Hz, effectively monitoring the DC component of the tail of the signal; and Construct a linear estimator that uses multiple parameters associated with various features of the resulting current signal. The outcome in designing a linear estimator is that the information contained in various parameters is weighted in such a way as to minimize the RMS error between the glucose concentration calculated by the estimator's equation and the actual glucose concentration that is present in the blood sample.

Accordingly, a linear estimator was constructed as follows:

The first parameter of the estimator was selected to be the real part of the first FFT coefficient (which corresponds to 0 Hz) of the tail of the signal (see FIG. 16) given by $Y_{Tail}$;

The second parameter was selected to be the real part of the first FFT coefficient of the head of the signal (which corresponds to 0 Hz), given by $Y_{headr}(0)$. In all cases with real signals, the imaginary part of the 0 Hz Fourier component is always 0; therefore, this parameter is not used.

The third parameter was selected to be the real part of the second FFT coefficient of the head of the signal (which corresponds to 0.048 Hz), given by $Y_{headr}(0.048)$; and The fourth parameter was selected to be the imaginary part of the second FFT coefficient of the head of the signal (which corresponds to 0.048 Hz), given by $Y_{headi}(0.048)$; and Subsequent parameters were selected by alternating between the real and imaginary parts of the FFT value for successively higher frequency components in the head of the signal until the maximum number of parameters is reached, in accordance with step 205. The optimal number of parameters to be used in constructing the linear estimator is identified here by using the randomized cross validation method to find the number of parameters that gives the lowest RMS as discussed above (see FIG. 18).

Figure 17:
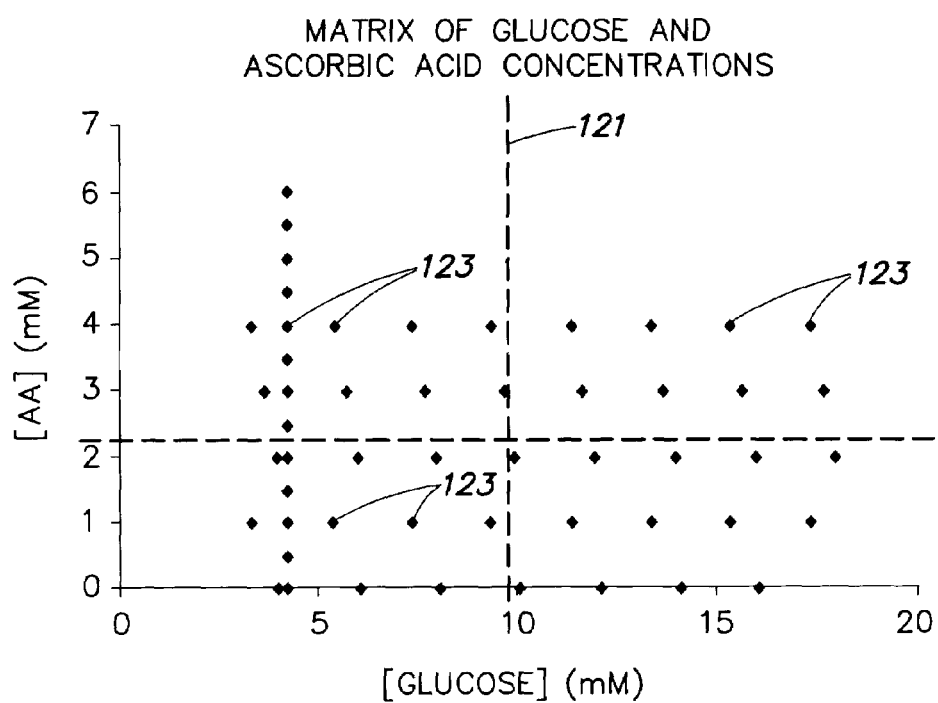
FIG. 17 shows a set of data points used as test data to train the estimator in the second illustrative example.

Thus, in this example, a set of 53 data points was collected, corresponding to several different combinations of glucose and ascorbic acid concentrations. The concentration combination data points 123 were plotted on a Cartesian coordinate system as shown in FIG. 17. This plane was then split into 4 sections as shown by the dashed line grid 121. The total data set is split roughly into two subsets, where one set is used in training the estimator (that is, one subset is used to determine the weights associated with each parameter in the linear estimator) and the other subset is used to test the performance of the newly constructed estimator.

Within each of the four sections of the plane, half of the points were randomly selected as the training subset and the remainder as the testing subset. Using this grid, the random selection is ensured to be more evenly distributed across the total set of data points, thereby minimizing the risk that some randomly selected training subsets are clustered, resulting in a badly trained estimator.

Using a two-parameter linear estimator, that is, one constructed using $Y_{tail}$ and $Y_{headr}(0)$, the associated weights of the parameters were calculated using data from the training set in accordance with linear estimation theory (step 230). The newly constructed estimation equation was then used to estimate the glucose concentrations of the remaining testing subset (step 235). After the RMS error of the estimated versus actual concentrations was computed, a different random subset of training and testing data was selected from the same total data set. These steps were repeated 1000 times, where each time, a different subset was chosen as the training set and the testing set. The average RMS of the 1000 runs was then calculated. This process was repeated for each parameter, with one parameter added to the linear estimator for each iteration.

Figure 18:
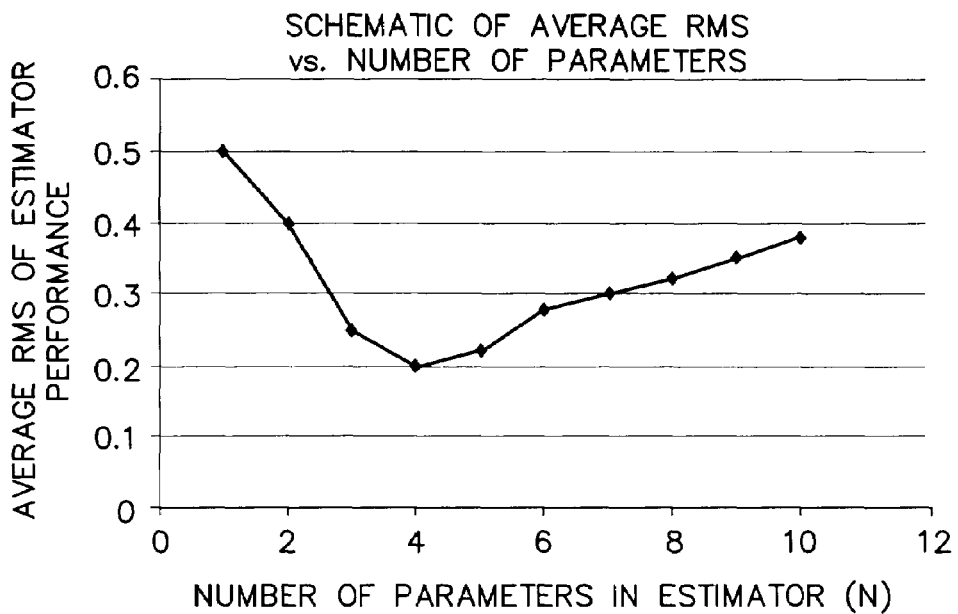
FIG. 18 is a schematic chart illustrating how the average RMS of the multi-parameter estimators could vary in accordance with the illustrative embodiment of FIG. 14.

FIG. 18 shows a schematic plot of typical results of the randomized analysis by plotting the number of parameters used in the estimator along the X-axis and the average RMS for that set of runs on the Y-axis. What is generally observed is that as the number of parameters increases, the RMS generally decreases. However, beyond a certain number of parameters, the RMS increases, indicating that too many parameters are used in the estimator, thereby constructing a less robust, and therefore, more error-prone estimation equation. Thus, by selecting the number of parameters that corresponds to the minimum RMS value, one can be assured of using the optimal number of parameters in constructing the estimator equation.

As indicated schematically in FIG. 18, it was found in this example that a four parameter estimator was the optimal construction:

$$[\text{Glucose}]=0.6Y_{headr}(0)-7.9Y_{headr}(0.048)+2.4Y_{headi}(0.048)+38.1Y_{Tail},$$

where $Y_{headr}(f)$ is the real part and $Y_{headi}(f)$ is the imaginary part of the Fourier Transform at frequency f, respectively, of the head of the measured signal, and $Y_{tail}$ is the real part of the 0 Hz Fourier Transform component of the tail of the signal.

Figure 19:
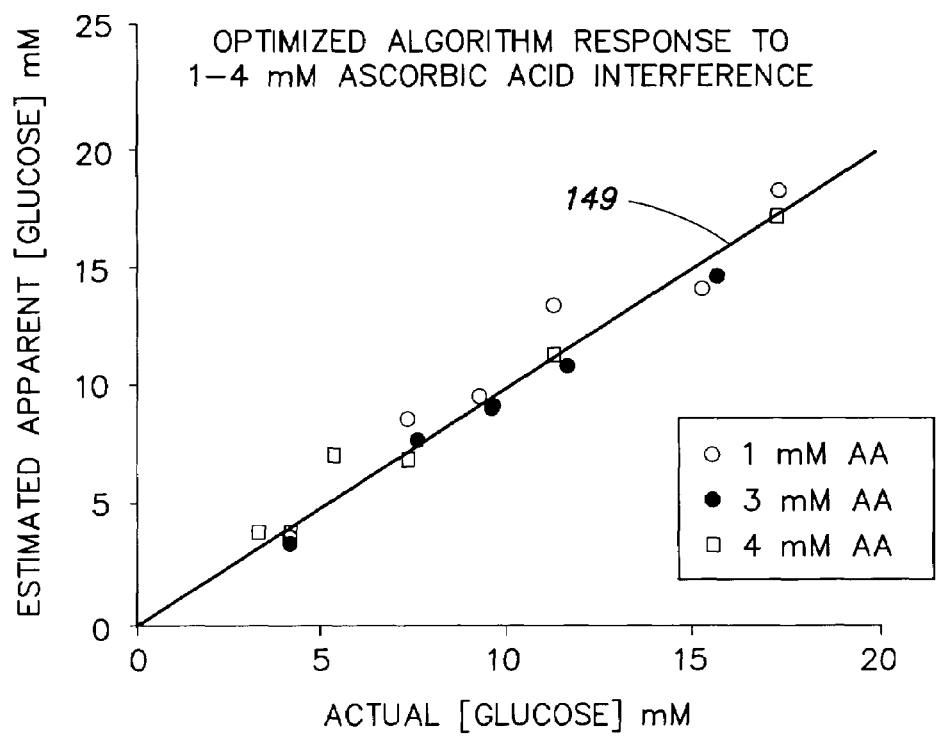
FIG. 19 is a chart showing the results of the second illustrative example.

Using this equation, various blood samples with mixed glucose and ascorbic acid concentrations were tested. Blood samples were prepared with known amounts of glucose and ascorbic acid. FIG. 19 shows the estimated glucose concentration calculated by using the [Glucose] equation above, versus the actual glucose concentration for samples that also contain various concentrations of ascorbic acid as an interferent.

Line 149 represents the actual glucose concentration. The open circles are measurements made in samples that have a background ascorbic acid concentration of 1 mM. The filled circles are measurements made in samples that have a background ascorbic acid concentration of 3 mM. The open squares are measurements made in samples that have a background ascorbic acid concentration of 4 mM.

Thus, for blood samples that contain glucose and a high concentration of ascorbic acid, the estimation equation was able to successfully suppress the signal from ascorbic acid and selectively measure the glucose part of the signal.

Figure 20:
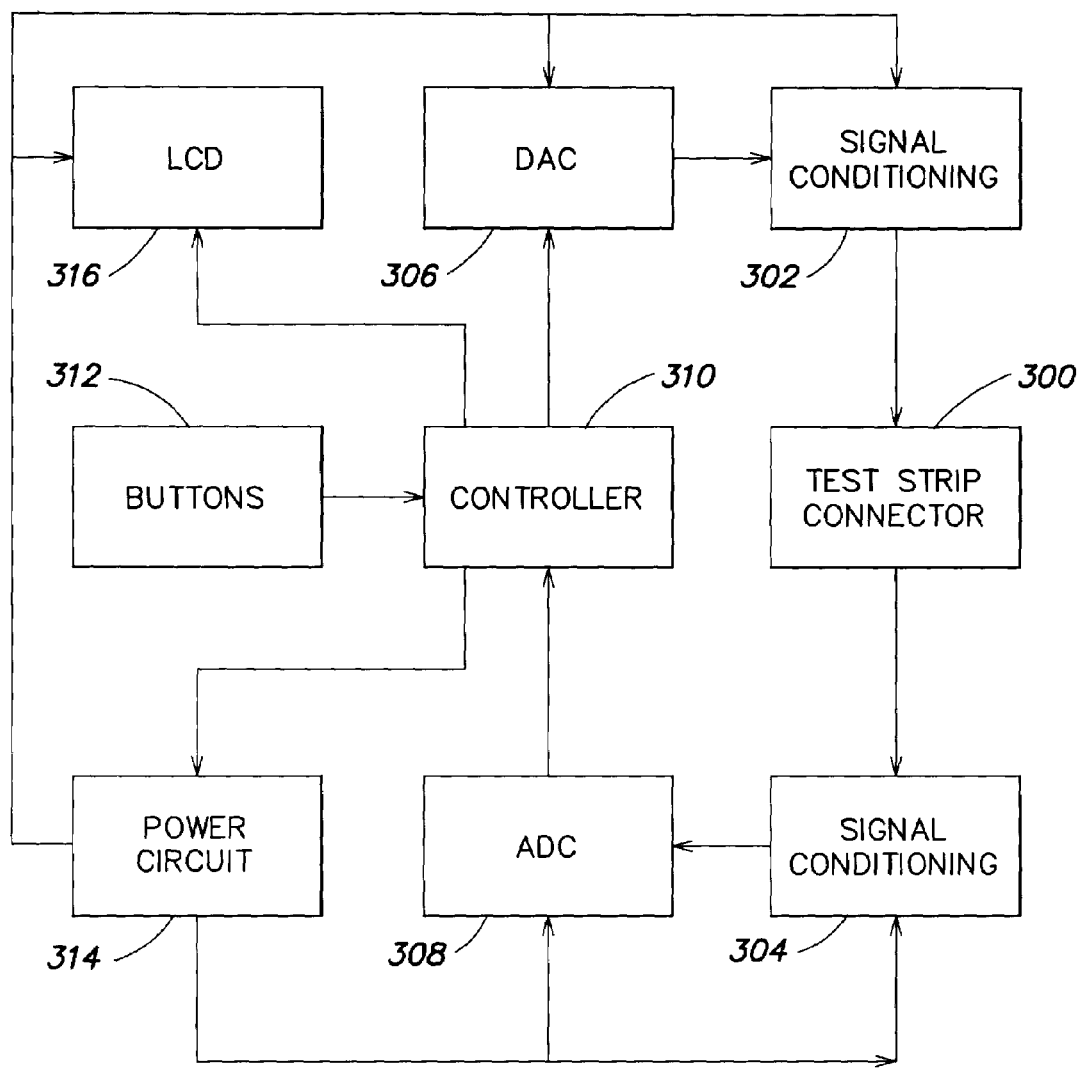
FIG. 20 is a glucose meter in accordance with another illustrative embodiment.

FIG. 20 shows an illustrative embodiment of a glucose meter used to implement the various methods described above. The meter includes a test strip connector 300 to connect the test-strip to the meter. The test strip can include, for example, three electrodes (working, reference, and counter).

Signal conditioning circuitry 302 is coupled to the test strip connector 300, and performs filtering of the waveform applied to the electrodes in the test strip. Signal conditioning circuitry 304 performs filtering of the resultant current signal from the test strip, and records the current signal. Circuitry 302 and 304 together comprise what is known as a potentiostat circuit. DAC 306 converts digital signals from controller 310 to analog signals. ADC 308 converts analog signals into digital format for use by controller 310. Controller 310 processes signals in the meter, for example, by processing current signals sensed by test strip connector in the manner taught in the foregoing illustrative embodiments of FIGS. 6 and 14.

Buttons 312 provide a user interface for the user to operate the meter. Power circuit 314 provides power to the meter, usually in the form of batteries, and LCD 316 displays the glucose concentration to the user.

It should be noted that the format of the FIG. 20 meter, and the signal processing systems and methods taught herein in FIGS. 5–19, can be used to sense analytes other than glucose. Such applications include: electrochemical immunoassay sensing, industrial gas sensing (e.g., cyanide gas while suppressing interference from hydrogen gas), water quality monitoring (biological or toxic metals), sensing of chemical and biological warfare agents.

The signal processing techniques taught herein can also be applied to existing sensing devices, such as a existing glucose testers. This modification can be in the form of a firmware upgrade to existing controllers. Examples of currently used controllers include Hitachi H8/3887, Texas Instruments 3185265-F, Sierra SC84036CV, Amtel S5640 ASIC, NEC FTA-R2 ACIC, Hitachi H8/3847, Panasonic MN101C097KB1, ASIC, (built around Intel 8051), etc.

The function of the firmware upgrade is to implement the following signal processing techniques taught herein:

1) Applying a customized waveform to the sample. The data that encodes the shape of the waveform will reside in memory, will be read by the microprocessor, and the desired waveform will be generated and applied to a digital to analog converter, e.g., DAC 306 of FIG. 20.

2) Read in the resulting current signal. The firmware will instruct the microprocessor to read in the digitized data from the analog to digital converter (sensed from the test strip electrodes), e.g., ADC 308 of FIG. 20, and store the digitized data in memory. The firmware will perform the memory management that is needed to read in the desired data.

3) Perform the mathematical operations to implement the signal processing. This includes calculating the parameters according to the firmware's instructions (e.g., compute the Fourier coefficients of the specified frequency components), and using these parameter values in the estimation equation (e.g., generated by the methods of FIG. 6 or FIG. 14) to determine the glucose concentration.

Other processes performed by the firmware may be left to the existing firmware and do not need to be part of the upgrade. For example, the firmware may also control the display of a result to the user (via the LCD 316 display, for example), and other "behind the scenes" operations of the meter, e.g., power management, respond to user requests such as scrolling of data, averaging of data, transferring data to a PC, etc.

It will be apparent to those skilled in the art that additional various modifications and variations can be made in the present invention without departing from the scope or spirit of the invention. For example, although a large amplitude stimulus waveform is used in the illustrative embodiments herein, a stimulus waveform having small signal characteristics can also be used to generate a nonlinear response.

Figure 21:
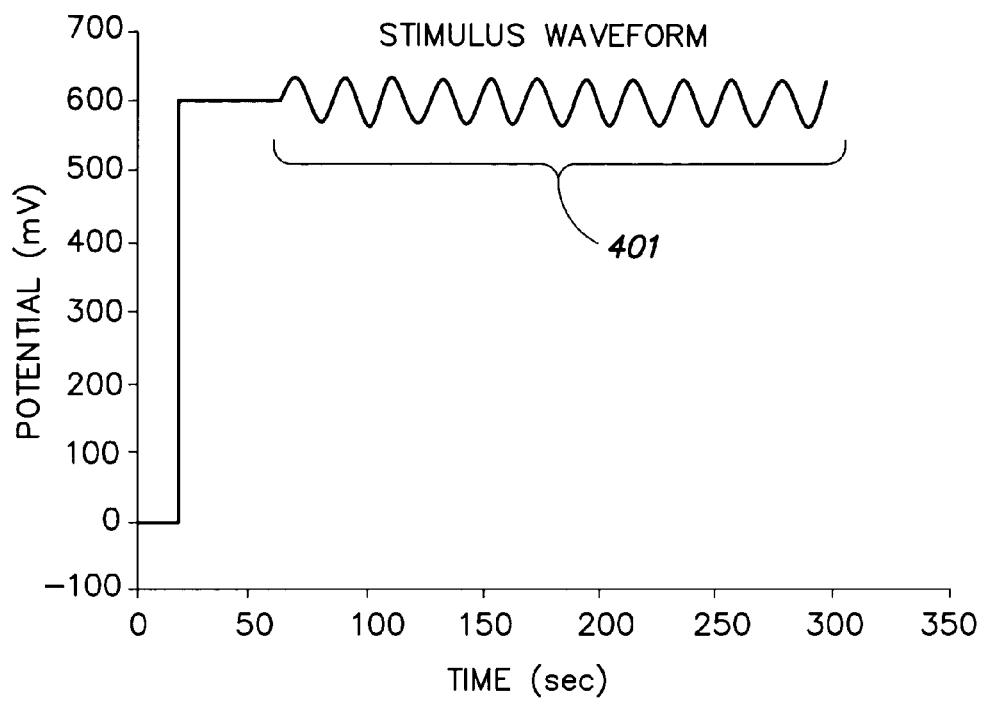
FIGS. 21 and 22 show an example of an alternative stimulus waveform and response, respectively.

An example of such a stimulus waveform is shown in FIG. 21, in which a step potential from 0 to 600 mV is applied. This stimulus can cause the resulting current signal to change from its equilibrium value at 0V to its new equilibrium value at 600 mV over the course of, for example, several seconds. During this transition of the current, as seen in portion 401 of the waveform, a small amplitude potential waveform (in this example a small amplitude sine wave) is superimposed over the signal. This would cause a small amplitude current response to occur on top of the slow transitioning current waveform.

Figure 22:
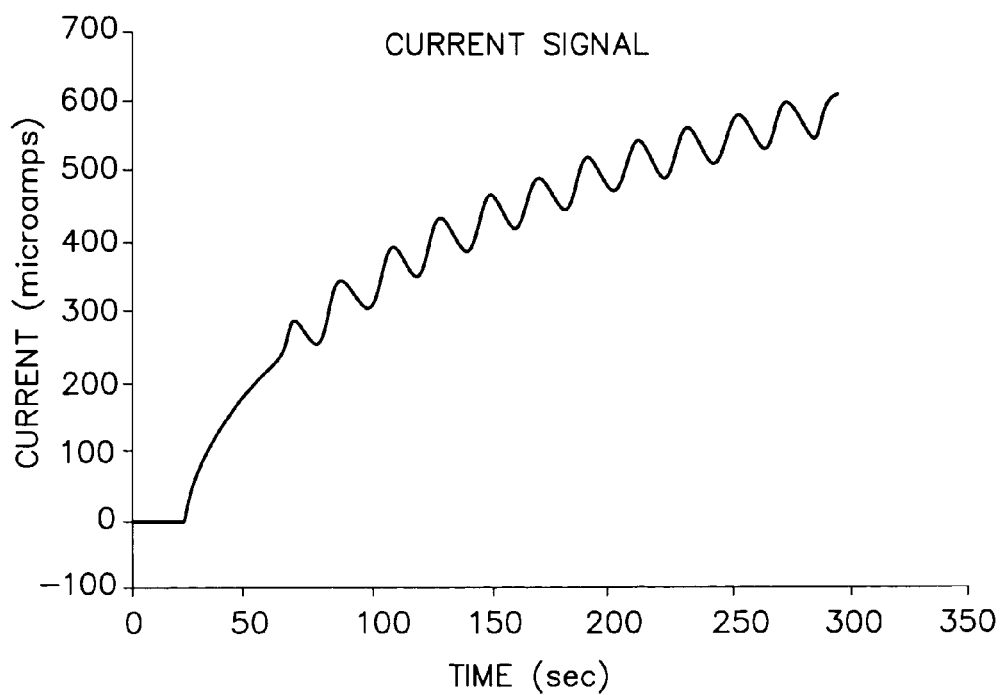

The total resulting current (that is, the relatively slow transitioning current plus the relatively fast sine wave current) shown in FIG. 22 would be nonlinear when compared to the applied sine wave potential. Thus, a large amplitude step potential causes the system to enter a transitioning state, but while in the transitioning state, a small amplitude potential is applied.

Referring to the current response shown in FIG. 22, it is observed that once the step potential is applied at 20 seconds, the current signal takes some time to re-equilibrate. During this transient re-equilibration period, the small amplitude sine wave potential is applied (starting at 65 secs). It is observed that from 65 seconds onwards, only a small amplitude signal is applied, but the resulting current is nonlinear since the resulting current contains multiple frequency components, illustrating one example of how a small amplitude waveform could result in a nonlinear signal response. Thus, this stimulus waveform would be useful in the illustrative embodiments disclosed herein.

The invention is also not limited to the use of any particular stimulus waveform, waveform shape or parameters. For example, a potentiometric method in which a current is the applied stimulus waveform and the measured potential is the resulting signal could be used. One or more of the following non-limiting examples could also be used:

Values of the measured and/or stimulus signal at some point in time;
Computed functions of all or some portion of the measured and/or stimulus signal, for example:
Slope of the signal at a point or slope of some portion of the signal;
Decay rate over some portion of the signal;
Rise rate over some portion of the signal;
Average value of some portion of the signal;
Frequency transform (e.g., Fourier transform, or wavelet transform) of all or some portion of the signal;
Logarithm of some portion of the signal;
Some root (e.g., square root or cube root) of some portion of the signal);
Some portion of the signal raised to some power;
Time elapsed between two specified points in the signal (e.g., time between a peak and a valley in the signal);
Combinations of these parameters, for example:
Decay rate of the signal during some interval of time divided by the average value of the signal during this interval;
Difference in value of the signal between two specified points;
Difference in slopes of the signal between two different portions of the signal;
A periodic stimulus to generate a periodic measured signal.

Additionally, cyclic voltammetry is not the only method to extract information about the reaction kinetics/mechanism and transport properties. Many different electroanalytical techniques can be used, such as: linear sweep voltammetry, square wave voltammetry, AC polarography, AC impedance spectroscopy, potentiometry, etc.

Further still, although the foregoing illustrative embodiments are primarily concerned with determining the concentration of one analyte of interest, e.g., glucose, it is apparent that the embodiments taught herein can be used to sense multiple analytes. In fact, when the estimation equations are constructed and solved, all the analytes can be quantified, even if only one concentration is displayed to the user. Additionally, estimation equations can be constructed for each analyte in a sample in the manner taught herein.

Non-Faradaic signals can also be measured as opposed to just Faradaic signals. For example, capacitive currents that are caused by reorganization of ions in the sample in response to a varying electrode potential could be all or part of the measured signal.

The stimulus waveform signal can be various quantities other than voltage and current that vary as a function of time, and thus result in a time varying measured signal. Such signals include:

Temperature of the sample;
Rotation rate of the electrode (varied at different speeds in the sample). The rotation of the electrode causes the sample to move in a vortex-type pattern, bringing more analyte into contact with the electrode. Varying the rotation rate as a function of time is a common way of probing transport properties of the analyte;
Light Varying the intensity of the light could be used to vary reaction rates and thus induce different analytes to generate different signals.

Also, multiple electrodes can be used instead of one electrode at a time, e.g., in an electrode array.

Other embodiments of the invention will be apparent to those skilled in the art from consideration of the specification and practice of the invention disclosed herein. It is intended that the specification and examples be considered as exemplary only, with a true scope of the invention being indicated by the following claims.

What is claimed is:

1. In an electrochemical method for monitoring of a select analyte in a mixed sample with an interfering analyte, the improvement comprising: applying a large amplitude potential stimulus waveform to the sample to generate a nonlinear current signal; and resolving a signal contribution from the select analyte in the generated signal by a vector projection method with an analyte vector comprising a plurality of real and imaginary parts of one or more Fourier coefficients at one or more frequencies of a reference current signal for the select analyte.

2. An electrochemical method of determining concentration of a select analyte in a mixed sample with an interfering analyte, comprising: applying a large amplitude potential stimulus waveform to the sample to generate a nonlinear current signal; measuring the generated signal; computing at least one parameter of all or some portion of the generated signal; and determining a concentration of the select analyte in the mixed sample by resolving an estimation equation based on analyte vectors for each of the select and interfering analytes and the at least one parameter.

3. The method of claim 2, wherein the estimation equation is based on analyte vectors at one frequency.

4. The method of claim 2, wherein the estimation equation is based on analyte vectors at multiple frequencies.

5. The method of claim 2, wherein one or both of the analyte vectors and the at least one parameter are weighted.

6. The method of claim 2, wherein the analyte vectors are comprised of the at least one parameter and relate to different portions of the stimulus waveform and/or generated signal.

7. The method of claim 2, wherein the analyte vectors are comprised of the at least one parameter and relate to at least one of a non-periodic portion and a DC portion of the stimulus waveform and/or generated signal.

8. The method of claim 2, wherein the estimation equation is based on a plurality of the at least one parameter selected from the group consisting of: one or more real or imaginary parts of a Fourier coefficient at one or more frequencies; one or more weighted real or imaginary parts of a Fourier coefficient at one or more frequencies; one or more portions of the stimulus waveform and/or generated signal; one or more periodic portions of the stimulus waveform and/or generated signal; one or more non-periodic portions of the stimulus waveform and/or generated signal; and one or more DC portions of the stimulus waveform and/or generated signal.

9. The method of claim 2, wherein the estimation equation is based on a select number of the at least one parameter to balance performance and robustness.

10. The method of claim 2, wherein the select analyte is glucose.

11. The method of claim 10, wherein the interfering analyte is ascorbic acid.

12. An apparatus comprising: a potentiostat circuit for applying a voltage waveform to and detecting a resulting current from an electrode system; at least one memory having program instructions and a processor configured to execute the program instructions to perform the operations of: applying a large amplitude potential stimulus waveform to the sample to generate a nonlinear current signal; measuring the generated signal; computing at least one Fourier coefficient of a desired frequency component of all or some portion of the generated signal; and determining a concentration of the select analyte in the mixed sample by use of the at least one Fourier coefficient to resolve an estimation equation based on analyte vectors for each of the select and interfering analytes.

13. A method of constructing an estimation equation for monitoring a select analyte in a mixed sample with an interfering analyte, the method comprising: selecting a large amplitude potential stimulus waveform to generate a nonlinear current signal When applied to the sample; applying the waveform to samples containing multiple different concentrations of each of the select and interfering analytes alone, and measuring the resulting reference current signals; computing values of real and imaginary parts of a Fourier transform for each of the reference current signals; plotting the real and imaginary values of a Fourier coefficient of the Fourier transform at each of a multiple number of frequencies; selecting one of the multiple frequencies at which the real and imaginary parts exhibit a relatively larger difference in phase angle; computing analyte vectors for each of the select and interfering analytes at the selected one frequency; and constructing the estimation equation based on the analyte vectors and calibration information that relates a concentration of the respective analyte in the sample to a length of the respective analyte vector in a complex plane.

14. The method of claim 13, wherein the waveform is selected based on theoretical and/or experimental factors.

15. The method of claim 14, wherein the factors reflect one or more of reaction kinetics, reaction mechanism and transport properties of the select and/or interfering analyte.

16. The method of claim 13, wherein the waveform is selected based on cyclic voltammetry to determine a potential at which the select and/or interfering analyte will oxidize or reduce.

17. The method of claim 13, wherein the waveform has a greater than 50 mV variation.

18. The method of claim 13, wherein the waveform or some portion of the waveform has a selected rate of variation based on one or more of a reaction kinetics, reaction mechanism and transport properties involving the select and/or interfering analyte.

19. The method of claim 13, wherein the waveform is selected to generate a Faradaic current signal arising from an electrochemical reaction of the select and/or interfering analyte.

20. An electrochemical method of determining concentration of a select analyte in a mixed sample with an interfering analyte, comprising: applying a stimulus waveform to the sample to generate a nonlinear signal; measuring the generated signal; computing at least one parameter of all or some portion of the generated signal; and determining a concentration of the select analyte in the mixed sample by resolving an estimation equation based on analyte vectors for each of the select and interfering analytes and the at least one parameter, wherein the at least one parameter is a frequency-domain parameter and/or a time-domain parameter.

21. The method of claim 20, wherein, the at least one parameter and/or analyte vectors are weighted.

22. The method of claim 20, wherein the stimulus waveform is a potential or a current waveform.

23. The method of claim 20, wherein the analyte vectors and the at least one parameter relate to different portions of the generated signal and/or stimulus waveform.

24. The method of claim 20, wherein the at least one parameter includes one or more of: values of the generated signal and/or stimulus waveform (hereinafter "the signal") at some point in time; computed functions of all or some portion of the signal, including one or more of: slope of the signal at a point or slope of some portion of the signal; decay rate over some portion of the signal; rise rate over some portion of the signal; average value of some portion of the signal; frequency transform of all or some portion of the signal; logarithm of some portion of the signal; some root of some portion of the signal; some portion of the signal raised to some power; time elapsed between two specified points in the signal; combinations of the parameters, including one or more of: decay rate of the signal during some interval of time divided by the average value of the signal during this interval; difference in value of the signal between two specified points; and difference in slopes of the signal between two different portions of the signal.

25. The method of claim 20, wherein the analytes are one or more of: glucose, an enzyme, hydrogen peroxide, a mediator, ferricyanide, ferrocene, ferrocyanide, ascorbic acid, uric acid, acetaminophen, and dopamine.

26. The method of claim 20, wherein the method includes monitoring multiple analytes.

27. The method of claim 20, wherein the applied waveform and generated signal are implemented with a galvanostat circuit or a potentiostat circuit.

28. The method of claim 20, wherein the at least one parameter is selected based on one or more of: separation of the analyte vectors; noise in the generated signal; and sensitivity of the generated signal at the analyte concentration.

29. The method of claim 20, wherein the estimator equation is further based on calibration information.

30. The method of claim 20, wherein the at least one parameter is selected based on one or more of: cyclic voltammetry; linear sweep voltammetry; square voltammetry; AC polarography; and AC impedance spectroscopy.

31. The method of claim 20, wherein the stimulus waveform is a current and the generated signal is a potential.

32. The method of claim 20, wherein the estimation equation is a linear estimator.

33. The method of claim 20, wherein the estimation equation is selected based on an estimation error determined by one or more of root mean squared (RMS), adjusted RMS, variance and standard deviation.

34. The method of claim 20, wherein the interfering analyte contributes a capacitive current to the generated signal.

35. The method of claim 20, wherein the stimulus waveform is applied to one or multiple electrodes.

36. An electrochemical method of determining concentration of a select analyte in a mixed sample with an interfering analyte, comprising: applying a stimulus waveform to the sample to generate a nonlinear signal; measuring the generated signal; computing at least one parameter of all or some portion of the generated signal; and determining a concentration of the select analyte in the mixed sample by resolving an estimation equation based on analyte vectors for each of the select and interfering analytes and the at least one parameter, wherein the stimulus waveform is a current and the generated signal is a potential.

* * * * *